(12) United States Patent
Tran et al.

(10) Patent No.: US 11,447,768 B2
(45) Date of Patent: Sep. 20, 2022

(54) MOLECULAR CELL DIARY SYSTEM

(71) Applicant: University of Florida Research Foundation, Incorporated, Gainesville, FL (US)

(72) Inventors: David Tran, Gainesville, FL (US); Son Le, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 494 days.

(21) Appl. No.: 16/078,272

(22) PCT Filed: Mar. 1, 2017

(86) PCT No.: PCT/US2017/020117
§ 371 (c)(1),
(2) Date: Aug. 21, 2018

(87) PCT Pub. No.: WO2017/151719
PCT Pub. Date: Sep. 8, 2017

(65) Prior Publication Data
US 2019/0055543 A1    Feb. 21, 2019

Related U.S. Application Data

(60) Provisional application No. 62/301,813, filed on Mar. 1, 2016.

(51) Int. Cl.
*A01N 63/00* (2020.01)
*C07H 21/04* (2006.01)
*C12N 15/10* (2006.01)
*C12N 15/85* (2006.01)
*C12N 15/90* (2006.01)
*A01K 67/027* (2006.01)
*C12N 15/63* (2006.01)
*C12N 9/12* (2006.01)
*C12N 9/22* (2006.01)
*C12Q 1/6886* (2018.01)

(52) U.S. Cl.
CPC ...... *C12N 15/1024* (2013.01); *A01K 67/0275* (2013.01); *C12N 9/1252* (2013.01); *C12N 9/22* (2013.01); *C12N 15/102* (2013.01); *C12N 15/63* (2013.01); *C12N 15/85* (2013.01); *C12N 15/90* (2013.01); *C12Q 1/6886* (2013.01); *C12Y 207/07007* (2013.01); *C12N 2800/80* (2013.01); *G01N 2800/7028* (2013.01)

(58) Field of Classification Search
CPC ........ C12N 15/79; C12N 15/85; C12N 15/90; C12N 2510/00; C12N 2310/20; C07H 21/02; C07H 21/04; C12Y 207/07007
See application file for complete search history.

(56) References Cited

U.S. PATENT DOCUMENTS

| | | |
|---|---|---|
| 2005/0106149 A1 | 5/2005 | Prusiner et al. |
| 2005/0255095 A1 | 11/2005 | Kakkis |
| 2014/0206546 A1 | 7/2014 | Chenchik |
| 2014/0349400 A1 | 11/2014 | Jakimo et al. |
| 2014/0356867 A1* | 12/2014 | Peter et al. |
| 2016/0106439 A1* | 4/2016 | Menashe |
| 2016/0208243 A1* | 7/2016 | Zhang et al. |
| 2016/0355879 A1* | 12/2016 | Kamberov et al. |
| 2017/0298450 A1* | 10/2017 | McManus |

OTHER PUBLICATIONS

Aubel, D. et al., *Watch the Clock—Engineering Biological Systems to Be On Time*, Current Opinion in Genetics & Development 20 (2010 634-643.
Blanpain, C. et al., *Unravelling Stem Cell Dynamics By Lineage Tracing*, Nature Reviews, Molecular Cell Biology, vol. 14 (Aug. 2013) 489-502.
Blundell, J. R. et al., *Beyond Genome Sequencing: Lineage Tracking With Barcodes To Study The Dynamics of Evolution, Infection, and Cancer*, Genomics 104 (2014) 417-430.
Bogdanove, A. J. et al., *TAL Effectors: Customizable Proteins for DNA Targeting*, Science, vol. 333 (Sep. 30, 2011) 1843-1846.
Bonnet, J. et al., *Rewritable Digital Data Storage in Live Cells Via Engineered Control of recombination Directionality*, PNAS, vol. 109, No. 23 (Jun. 5, 2012) 8884-8889.
Bystrvkh, L. V. et al., *Barcoded Vector Libraries and Retroviral or Lentiviral Barcoding of Hematopoietic Stem Cells*, Chapter 23, Hematopoietic Stem Cell Protocols, Methods in Molecular Biology, vol. 1185 (2014, pp. 345-360.
Danino, T. et al., *A Synchronized Quorum of Genetic Clocks*, Nature, vol. 463 (Jan. 2010) 326-330.

(Continued)

*Primary Examiner* — Shin Lin Chen
(74) *Attorney, Agent, or Firm* — Alston & Bird LLP

(57) ABSTRACT

The subject invention pertains to a Molecular Cell Diary System (MCDS), which allows identification of the history of somatic alterations in the cell. MCDS comprises one or more combinations of a DNA cutter and a DNA writer expressed under the control of a promoter controlled a cellular event of interest. The DNA cutter and the DNA writer are in a combination are co-expressed when an even of interest occurs. The DNA cutter creates double strand breaks (DSB) in a target DNA in a sequence specific manner and the DNA writer incorporates DNA sequences in the DSB. The endogenous DNA repair machinery synthesizes repairs the DSB. As such, the combination of the DNA cutter and the DNA writer modifies the target DNA and leaves "marks" of the occurrence of the cellular event of interest. These marks are sequenced and the cellular event history of the cell is deciphered.

22 Claims, 23 Drawing Sheets

Specification includes a Sequence Listing.

(56) References Cited

OTHER PUBLICATIONS

Farzadfard, F. et al., *Genomically Encoded Analog Memory With Precise In vivo DNA Writing in Living Cell Populations*, Science, vol. 346, Issue 6211 (Nov. 14, 2014) 825 and 1256272-1-8.

Fowler, J. D. et al., *Biochemical, Structural, and Physiological Characterization of Terminal Deoxynucleotidyl Transferase*, Chem. Rev. 106 (2006) 2092-2110.

Friedland, A. E. et al., *Synthetic Gene Networks That Count*, Science, vol. 324 (May 29, 2009) 1199-1202.

Glaser, J. I. et al., *Statistical Analysis of Molecular Signal Recording*, PLOS Computational Biology, vol. 9, Issue 7 (Jul. 2013) 1-14.

Goldbeter, A. et al., *Systems Biology of Cellular Rhythms*, FEBS Letters 586 (2012) 2955-2965.

Inniss, M. C. et al., *Building Synthetic Memory*, Current Biology, vol. 23, No. 17 (Sep. 9, 2013) RB12-RB16.

Kim, H. et al., *A Guide to Genome Engineering With Programmable Nucleases*, Nature Reviews, vol. 15 (May 2014) 321-334.

Kleinstiver, B. P. et al., *Engineered CRISPR-Cas9 Nucleases With Altered PAM Specificities*, Nature, vol. 523 (Jul. 23, 2015) 481-485; also pp. a-1.

Kording, K. P., *Of Toasters and Molecular Ticker Tapes*, PLOS Computational Biology, vol. 7, Issue 12 (Dec. 2011) 5 pages.

Kuhn, R. et al., *Inducible Gene Targeting in Mice*, Science, vol. 269 (Sep. 8, 1995) 1427-1429.

Levy, S. F. et al., *Quantitative Evolutionary Dynamics Using High-Resolution Lineage Tracking*, Nature, vol. 519 (Mar. 12, 2015) 181-186; also pp. a-c.

Masutomi, K. et al., *Telomerase Activity Reconstituted in Vitro With Purified Human Telomerase Reverse Transcriptase and Human Telomerase RNA Component*, The Journal of Biochemistry, vol. 275, No. 29 (Jul. 21, 2000) 22568-22573.

McKenna, A. et al., *Whole-Organism Lineage Tracing By Combinatorial and Cumulative Genome Editing*, Science, vol. 353, Issue 6298 (Jul. 29, 2016), 462; also pp. aaf7907-l-aaf7907-11.

Motea, E. A. et al., *Terminal Deoxynucleotidyl Transferase: The Story of a Misguided DNA Polymerase*, Biochimica et Biophysica Acta 1804 (2010) 1151-1166.

Nandakumar, J. et al., *Finding The End: Recruitment of Telomerase To The Telomere*, Nat Rev Mol Cell Biol. 14(2) (Feb. 2013) 69-82.

Nimmo, R. A. et al., *Primed and ready: Understanding Lineage Commitment Through Single Cell Analysis*, Trends in Cell Biology, vol. 25, No. 8 (Aug. 2015) 459-467.

Palm, W. et al., *How Shelterin Protects Mammalian Telomeres*, Annu. Rev. Genet. 42 (2008) 301-334.

Pardue, M. et al., *Drosophila Telomeres: A Variation on the Telomerase Theme*, Landes Bioscience, Fly, 2:3 (May/Jun. 2008) 101-110.

Peliska, J. A. et al., *Mechanism of DNA Strand Transfer Reactions Catalyzed by HIV-1 Reverse Transcriptase*, Science, vol. 258 (Nov. 13, 1992) 1112-1118.

Purcell, O. et al., *Synthetic Analog and Digital Circuits for Cellular Computation and Memory*, Current Opinion in Biotechnology 29 (2014) 146-155.

Sanchez-Rivera, F. J. et al., *Application of the CRISPR-Cas9 System in Cancer Biology*, Nature Reviews, vol. 15 (Jul. 2015) 387-395.

Schatzl et al., *P-104: AR-12 and Its Derivatives, a Potential New Therapeutic Agent Against Prions*, Prior 2016 Poster Abstract, Prion, vol. 10, Suppl. 1 (Apr. 18, 2016) S37-S127.

Schmidt, J. C. et al., *Human Telomerase: Biogenesis, Trafficking, Recruitment, and Activation*, Genes & Development 29 (2015) 1095-1105.

Siuti, P. et al., *Synthetic Circuits Integrating Logic and Memory in Living Cells*, Nature Biotechnology, vol. 31, No. 5 (May 2013) 448-452; also p. a.

Stricker, J. et al., *A Fast, Robust and Tunable Synthetic Gene Oscillator*, Nature, vol. 456 (Nov. 27, 2008) 516-519; also p. a.

Tigges, M. et al., *A Tunable Synthetic Mammalian Oscillator*, Nature, vol. 457 (Jan. 15, 2009) 309-312.

Treutlein, B. et al., *Reconstructing Lineage Hierarchies of the Distal Lung Epithelium Using Single-Cell RNA-Seq*, Nature, vol. 509 (May 15, 2014) 371-375; also pp. a-k.

Tsai, S. Q. et al., *Dimeric CRISPR RNA-Guided FokI Nucleases For Highly Specific Genome Editing*, Nature Biotechnology, vol. 32, No. 6 (Jun. 2014) 569-576; also p. a.

Yamtich, J. et al., *DNA Polymerase Family X: Function, Structure, and Cellular Roles*, Biochimica et Biophysica Acta 1804 (2010) 1136-1150.

Zetsche, B. et al., *Cpf1 Is a Single RNA-Guided Endonuclease of a Class 2 CRISPR-Cas System*, Cell 163 (Oct. 22, 2015) 759-771.

Zhang, L. et al., *Retrotransposons at Drosophila Telomeres: Host Domestication of a Selfish Element for the Maintenance of Genome Integrity*, Biochimica et Biophysica Acta 1819 (2012) 771-775.

International Search Report and Written Opinion for Application No. PCT/US2017/020117 dated May 18, 2017, 12 pages.

\* cited by examiner

SEQUENCE LISTING

```
<160> NUMBER OF SEQ ID NOS: 1

<210> SEQ ID NO 1
<211> LENGTH: 11
<212> TYPE: DNA
<213> ORGANISM: Homo sapiens

<400> SEQUENCE: 1
cuaacccuaa c                                                          11
```

MOLECULAR CELL DIARY SYSTEM

CROSS-REFERENCE TO RELATED APPLICATION

This application claims the benefit of U.S. Provisional Application Ser. No. 62/301,813, filed Mar. 1, 2016, the disclosure of which is hereby incorporated by reference in its entirety, including all figures, tables and amino acid or nucleic acid sequences.

The Sequence Listing for this application is labeled "Seq-List.txt" which was created on Feb. 22, 2017 and is 1 KB. The entire content of the sequence listing is incorporated herein by reference in its entirety.

This invention was made with government support under CA160824 awarded by National Institutes of Health. The government has certain rights in the invention.

BACKGROUND OF THE INVENTION

Cells are the smallest independent unit of life. Every cell is different and makes its own decisions in every respect. However cells do not exist alone, but interact, collaborate, and compete with one another. Each cell carries with it the programs that control its fate, be it during development or in pathologic processes like cancer. Cells use a complex cascade of signaling programs to communicate with one another and to respond to cues from their microenvironment and other organs to stay alive and perform their intended functions.

However, the understanding of how these circuitries of signal-processing factors are harmoniously unified in the complex behaviors of cellular life is incomplete. The roles of different cells are studied from indirect experiments by either deleting genes or neutralizing gene products. The methods such as Omics and system biology generate a vast amount of data of potential forms-and-functions associations. However without direct biological relevance, these associations often create more questions than answers.

Cell fate determination is critical for cellular functions, from development, tissue repair and regeneration, to diseases like tissue fibrosis and cancer. Unfortunately it is poorly defined in many tissues and not readily discernable by studying terminally differentiated cells since the cell fate factors tend to be expressed transiently and early in the differentiation program. When tissue-specific fate factors are known, it is still necessary to know the sequence of events during the lineage commitment process. Fate signals often begin in a small number of cells, making it difficult to identify and isolate them.

Even if these rare early committed cells could be isolated and potential fate factors identified, determining which factor controls which lineage is challenging because the true fates become harder to ascertain after cells have been extracted. Moreover, the average population approach often masks the detailed circuitry of individual fate choices due to the averaging of cellular heterogeneity.

Although cancer can be viewed as a failed fate determination state, the cell origin of cancer remains unclear. Whether tumor-initiating cells originate from normal progenitor cells that become transformed or from differentiated cells that turn on the stemness program as they become transformed is not known. Tumors are composed not only of cancer cells but also, in a significant fraction, of stromal cells, which are thought to play critical roles in cancer progression. However the origin of tumor-associated stromal cells is also uncertain. Also, whether the tumor-associated stromal cells are the tissue resident stromal cells that are coopted by cancer cells is not known. Further, whether the tumor-associated stromal cells are they descendants of tumor-initiating cells just like non-stem cancer cells is also not known. The tumor-associated stromal cells may even represent a transient state of cancer cells during tumor progression, for example, the cancer-associated fibroblasts may represent carcinoma cells actively undergoing the epithelial-mesenchymal transition. The tumor-associated stromal cells may also be circulating stromal cells that are actively recruited to the tumor. Discerning between these possibilities would lead to better therapies by targeting the interdependent networks of cancer cells and their tumor microenvironment.

Tumors are highly heterogeneous with multiple coexisting clones and subclones. Each clone possesses differential potentials for growth and metastasis at different stages of tumor progression, for example, primary tumor growth, EMT initiation and local invasion, migration to distant sites, dormancy of disseminated tumor cells (DTCs) in distant sites and finally reactivated growth, for example, mesenchymal-epithelial transition (MET) of dormant DTCs to form metastases. Which minimal changes in master regulators are necessary and sufficient at each transition point in the metastatic cascade is not known. Specifically, the driver mutations that endow a cancer cell the ability to initiate EMT and invade are not known. Also, somatic alterations in dormant DTCs required to reactivate growth are not known.

Tumor dormancy is a significant and poorly understood clinical problem. It is defined as the presence of cancer stem-like disseminated tumor cells (DTCs) that are clinically silent and evade therapy. Therapeutic strategies to eliminate dormant DTCs have been elusive because of their rarity and a dearth of actionable targets.

Cell-extrinsic factors such as the DTC niche, immunity and angiogenesis are important in tumor dormancy. From the cell-intrinsic standpoint, dormant DTCs share several parallels with cancer stem-like cells, with overactive survival and stress-induced p38MAPK pathways and epithelial-mesenchymal transition (EMT) (FIG. 6). DTCs can arise from premalignant lesions (early DTCs) and established tumors (late DTCs). Early and late DTCs appear to differ in their potential for dormancy maintenance and eventual reactivation of growth with early DTCs tending to have longer dormancy period, presumably due to their arising from lesions with lower burden of somatic changes compared to late DTCs. Therapeutic success will depend on the ability to target both DTC populations, which requires identifying all driver somatic alterations at each DTC milestone (i.e. emergence from primary tumor, migration, dormancy in secondary organs, and MET to form macrometastases).

A records-keeping system would be beneficial that chronicles events in vivo in real time and provides a temporal and dynamic picture of fate determining events in individual cells without having to isolate them from the system. Current technologies only allow for identifying a single type of cellular event. For example, lineage tracing can be done by fluorescently labeled proteins and fixed DNA barcoding. An example of fluorescent protein-based lineage tracing is the recently developed BRAINBOW technique in which hundreds of different color hues were generated by randomly combining a limited set of different fluorescent proteins and used to label distinct neuronal lineages to study brain organogenesis. The main drawback of this process is the modest resolution due to limited numbers (usually hundred) of non-overlapping color hues that can be generated.

Fixed DNA barcoding has far more coding capacity, which in one study could distinguish up to 500,000 different cell lineages. However, the fixed DNA barcoding does not provide parental information of lineage conforming cells since all cells in a lineage carry the same barcode.

The US patent application publication US2015/0225801 describes a method for lineage mapping and molecular events recording in individual cells in which random deletion mutations were introduced into presynthesized genetic scratchpads that contained fixed DNA barcodes. By analyzing mutational patterns in these scratchpads, lineage trees can be deduced. However, in this system, the ability to accurately measure the number of events is limited because there is no method to delineate the number or pattern of mutations written onto a scratchpad per event. In addition, this system does not allow cell activity dynamics recording.

Other systems containing a biological clock or event counter like the riboregulated transcription cascade, that record event dynamics such as the molecular ticker tape based on nucleotide misincorporation patterns and the recombinase-based single stranded DNA tape recorder, are inefficient and do not allow lineage tracing.

BRIEF SUMMARY OF THE INVENTION

The invention provides a system, herein referred to as a Molecular Cell Diary System (MCDS), which allows a single-cell analysis to identify somatic alterations that occurred in the cell to provide the history of molecular events that occurred in the cell. MCDS allows simultaneous assessment of multiple cellular characteristics, for example, 1) lineage identity of individual cells (i.e. lineage tracer); 2) number of cell divisions that has occurred (i.e. cellular clock); and 3) dynamic changes in biological processes such as EMT initiation (i.e. cellular barometer/memory).

The MCDS utilizes DNA writers to write DNA sequences, for example, short DNA sequences, for example, of about 50 to 300 bp, about 75 to 275 bp, about 100 to 250 bp, about 125 to 225, about 150 bp to 200 bp or about 150 bp, into specific genomic locations and link such writing events to the cellular events of interest. The specific genomic locations are double strand breaks (DSBs) created by a sequence specific nuclease, hereinafter referred to as "DNA cutter," that are also linked to the cellular events of interest.

As such, the MCDS comprises a combination of a DNA cutter and a DNA writer expressed under the control of a promoter, wherein the promoter is controlled by the occurrence of a cellular event of interest. When the cellular event of interest occurs, the DNA cutter and the DNA writer are co-expressed. The DNA cutter creates double strand breaks (DSBs) in the genome of the cell in a sequence specific manner and the DNA writer writes DNA sequences at the positions of the DSBs. The endogenous DNA synthetic and repair machineries, for example, Non-homologous End Joining (NHEJ) pathway, synthesize the complementary strand to the "newly written" DNA sequence and seal the DSB. As such, the combination of the DNA cutter and the DNA writer modifies the DNA of the cell and leaves the "marks" of the occurrence of the cellular event of interest. These marks can be identified by DNA sequencing, for example, next-generation sequencing (NGS) at the single cell level, and the cellular event history of the cell can be deciphered (FIG. 1).

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

DETAILED DISCLOSURE OF THE INVENTION

Figure 1:
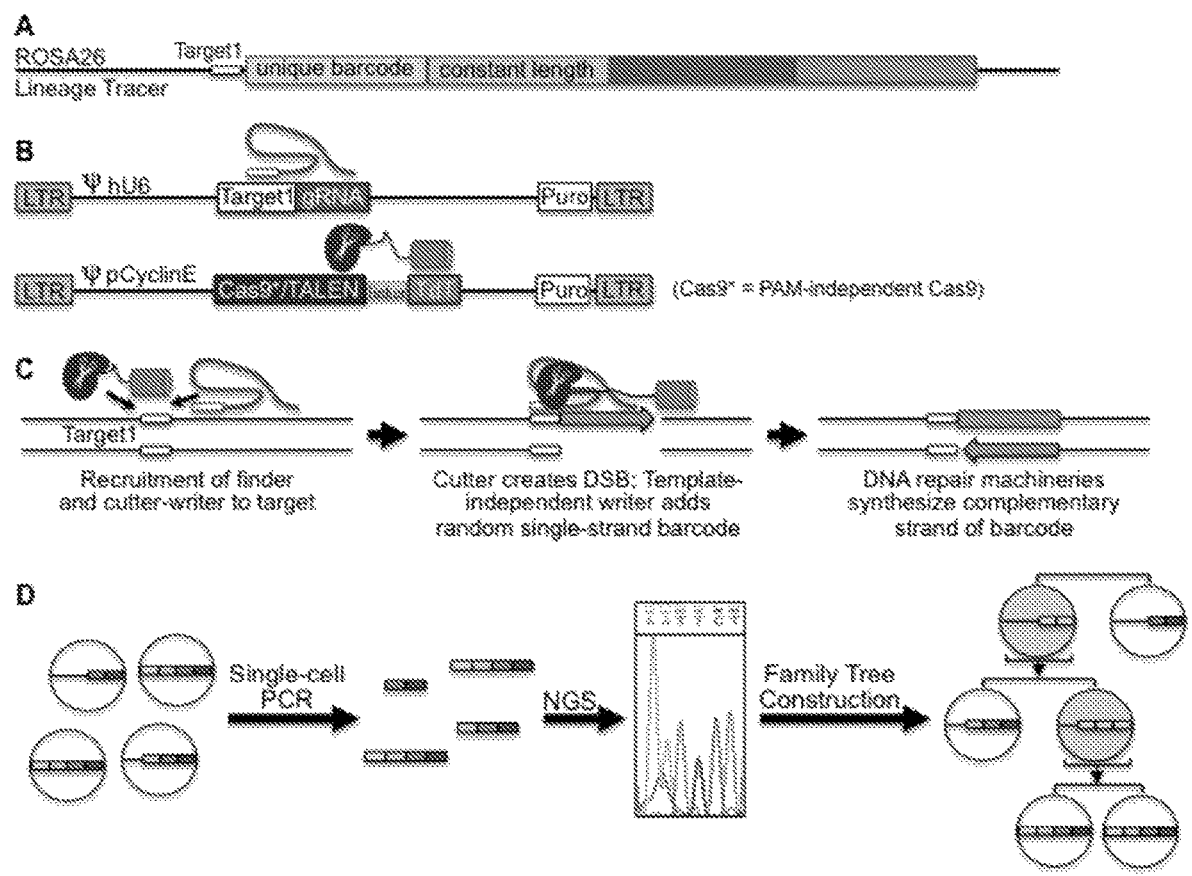
FIG. 1. A basic lineage tracer. (A) Diagram of recorded variable barcodes written on a predefined target site. Repeated events are recorded as concatenated random barcodes. (B) Components of a basic lineage tracer. The finder (guide RNA or gRNA) is expressed by a constitutively active hU6 promoter. The cutter (Cas9* or TALEN) is fused with the writer (TdT) by a flexible linker and under the control of the cyclin E promoter, which is active at the $G_1$-S transition of the cell cycle. Cas9*= a modified PAM-independent Cas9* that creates a blunt end DSB or a Cas9-related endonuclease such as Cpf1 that cuts downstream of the PAM sequence at nucleotide 18 on the forward strand and 23 on the reverse strand, thus creating a sticky end DSB (this version of Cas9* is referred to as PAM-retaining Cas9* or nuclease). (C) Schematic of a basic lineage tracer. The finder is recruited to the target site, which in turn recruits the curter-writer complex. The cutter creates a DSB in the DNA. The writer then adds a random single-strand sequence. The sequence length is the same as the length of the flexible linker. Endogenous DNA repair machineries then synthesize the complementary strand of the barcode and reseal the DSB. The process is repeated at each $G_1$-S transition. (D) Sample workflow of the lineage tracer. Genomic DNA isolated from single cells is subjected to PCR amplification of written barcodes. The PCR products are next subjected to NGS. A cellular family tree is then constructed based on the identity and order of random barcodes. Grayed out cells are parental cells that are no longer in existence.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0 to 20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of the lengths of nucleotide sequences, the terms "about" or "approximately" are used these lengths encompass the stated length with a variation (error range) of 0 to 10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0 1-1 0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range), specific embodiments therein are intended to be explicitly included.

As used herein, the term "cancer" refers to the presence of cells possessing abnormal growth characteristics, such as uncontrolled proliferation, immortality, metastatic potential, rapid growth and proliferation rate, perturbed oncogenic signaling, and certain characteristic morphological features. This includes but is not limited to the growth of: (1) benign or malignant cells (e.g., tumor cells) that correlates with overexpression of a serine/threonine kinase; or (2) benign or malignant cells (e.g., tumor cells) that correlates with abnormally high levels of serine/threonine kinase activity or lipid kinase activity. Non-limiting serine/threonine kinases implicated in cancer include but are not limited to PI-3K mTOR, and AKT. Exemplary lipid kinases include but are not limited to PI3 kinases such as PBK$\alpha$, PBK$\beta$, PBK$\delta$, and PBK$\gamma$.

"Subject" refers to an animal, such as a mammal, for example a human. The methods described herein can be useful in both humans and non-human animals. In some embodiments, the subject is a mammal (such as an animal model of disease), and in some embodiments, the subject is human.

For the purpose of the invention, the phrase, "the expression of a gene is activated by the occurrence of a cellular event of interest" indicates that the gene is under the control of a promoter, where the cellular event of interest results in the production of biomolecules, for example, transcription factors, that induce the expression of a gene under the control of the promoter, either directly or indirectly. For example, the transcription factors associated with the event of interest can recruit transcription machinery to the promoter thereby inducing the transcription of the gene under the control of the promoter. As such, the phrase, "the expression of the gene is activated by EMT" indicates that the gene is under the control of a promoter, where EMT results in the production of biomolecules, for example, transcription factors, that bind to the promoter, either directly or indirectly, and recruit transcription machinery to the gene thereby inducing the transcription of the gene under the control of the promoter activated by the occurrence of EMT.

As used herein, the phrase "a gene under the control of a promoter" indicates that the expression, i.e., the transcription of the gene, is controlled by the promoter. The expression of a gene under the control of a promoter is induced via biomolecules, for example, transcription factors, that bind to the promoter, either directly or indirectly, and recruit transcription machinery to the gene thereby inducing the transcription of the gene. An example of a gene under the control of a promoter is where the gene is linked to the promoter in a manner that allows for expression of the gene in a host cell when a construct comprising the gene and the promoter is introduced into the host cell. In such cases, the expression of the transcription factor activating the expression of a gene operably linked to a promoter is occurs with the cellular event of interest. For example, if an endogenous gene is under the control of an endogenous promoter, the event of interest is associated with the production of transcription factors that induce the expression of genes under the control of the endogenous promoters. Another example of a gene under the control of a promoter is where the gene is under the control of a promoter, wherein the promoter is activated by a biomolecule producing during the occurrence of the event of interest and wherein, the biomolecule activates the expression of the gene under the control of the promoter in an indirect manner, e.g., through other biomolecules, such as, trans-activators.

As discussed above, cell fate determination and cell-cell interactions determine how cells function in the interconnected environment of tissues, organs and organism. When dis-regulated, cells are the root cause of diseases including cancer. To understand these processes in vivo requires a system that allows for a comprehensive record of cellular life. The ability to determine generational relationship among cells within the same lineage and then to have their individual genetic or epigenetic profiles means that critical regulatory networks regulating fate transitions during the life of the cell can be pinpointed with higher accuracy and confidence. This in turn allows more focused biological validation experiments to proceed rapidly.

The MCDS of the invention provides enzymes that produce massively parallel historical compilation of cellular functions as specific DNA sequences in a cell's genome. MCDS is provides several advantages over existing methods, including: 1) A comprehensive all-in-one system that allows for simultaneous recording of information pertaining to cell lineages, biological timing, and cellular and molecular activity dynamics at the single cell level; 2) An ability to track large numbers of cells individually in vivo using random, unique barcodes of infinite variations coupled with massively parallel processing; and 3) A powerful tool to identify critical genetic and or epigenetic drivers of events of interest, as revealed when the reconstructed family tree, cell fate history and molecular activity history are aligned with data obtained from single cell analytical genomic tools.

In one embodiment, the MCDS of the invention provides a comprehensive and adaptive system that allows simultaneous assessment of multiple cellular characteristics, for example, 1) lineage identity of individual cells (i.e. lineage tracer); 2) number of cell divisions that has occurred (i.e. cellular clock); and 3) dynamic changes in biological processes such as EMT initiation (i.e. cellular barometer/memory). When coupled with single-cell genomics, MCDS provides unparalleled capacity to determine, in great detail, the genetic origin of a cell, timing of cellular events of interest (e.g. emergence of driver mutations during EMT initiation, dormant DTCs, and MET), and molecular differences among cells (e.g. early and late DTCs) and their interactions that underlie diverse potentials for different cellular outcomes (e.g. dormancy or MET). As such, MCDS provides deep understanding of an isolated cell, for example, a DTC, which in turn can be implemented for the development of novel therapeutic strategies against DTCs.

Figure 2:
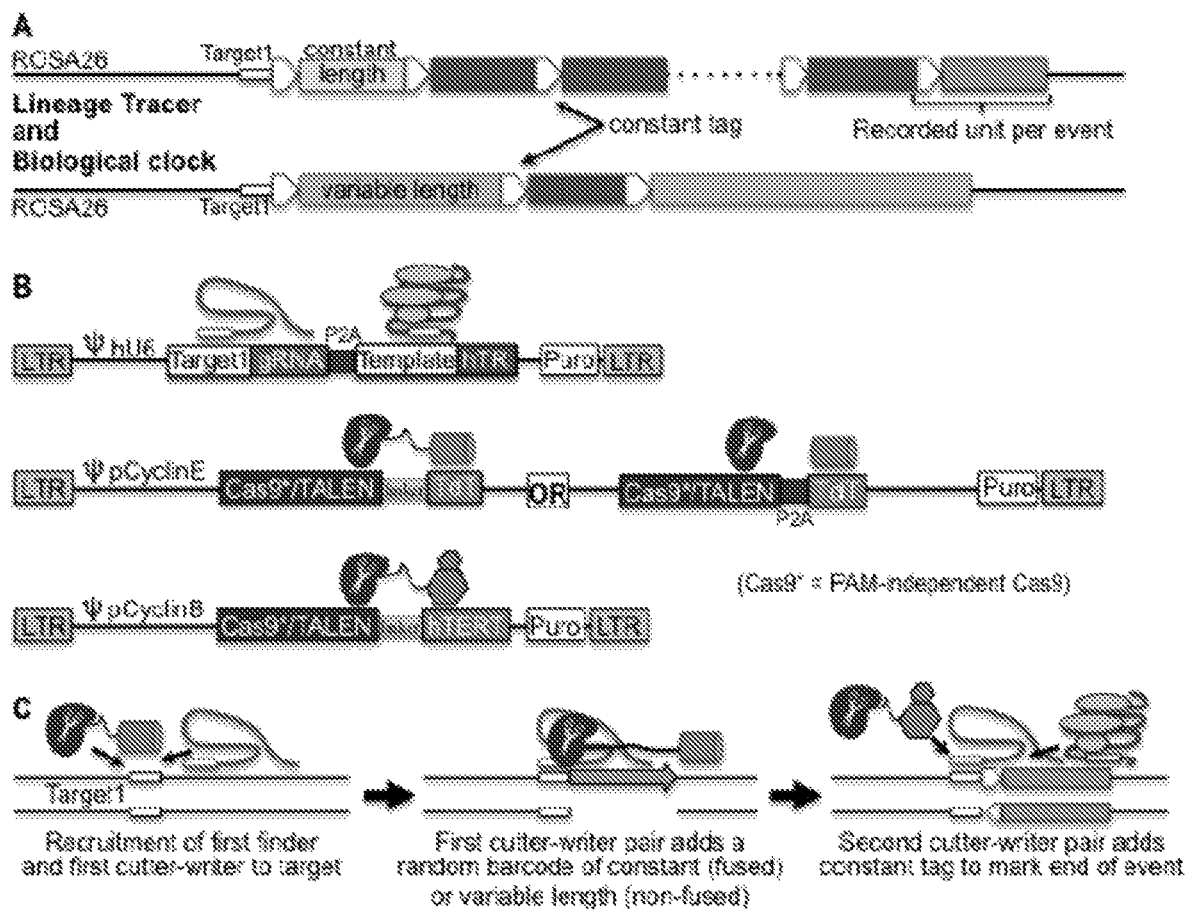
FIG. 2. (A) Diagram of recorded units of random unique barcode, either of constant length or variable length and a constant tag written on a predefined target site. Repeated events are recorded as concatenated units. (B) Constructs of MCDS components for a Lineage Tracer and Biological Clock. The Biological Clock uses temporally spaced cyclin E and cyclin B promoters driving the cutter (Cas9*/TALEN) fused to the writer TdT (random barcode) or hTERT (constant tag). If the writer is not fused to the cutter, the random barcodes will have variable lengths depending on the amplitude of activity of the driving promoter. (C) Schematic of the double function MCDS on the target DNA site.
Figure 3:
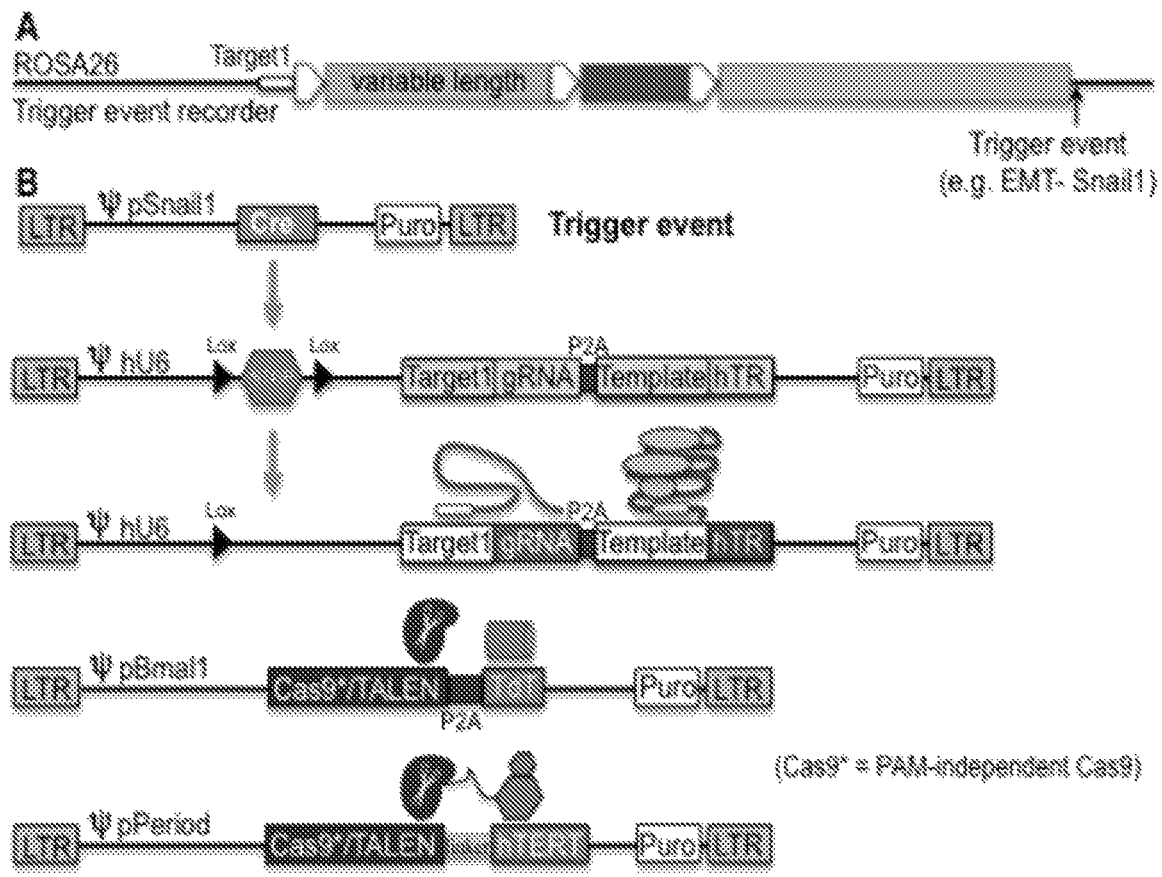
FIG. 3. A Single-Use On-Switch Trigger Event Recorder. (A) Diagram of recorded units of a single On-switch trigger event recorder as coupled with a reference biological clock (cell division cycle or circadian rhythm). (B) Constructs of components for a Trigger Event Recorder, e.g., EMT activation by SNAIL1. Upon EMT initiation, the SNAIL1 promoter is activated leading to Cre expression, which in turn excises the loxP-Stop-loxP cassette to turn on expression of the finders. The cutter and writers combinations are driven by promoters specific for oscillating phases of the circadian rhythm (Bmal 1 and Period). The triggered finders set off recording by oscillating cutter and writers.
Figure 4:
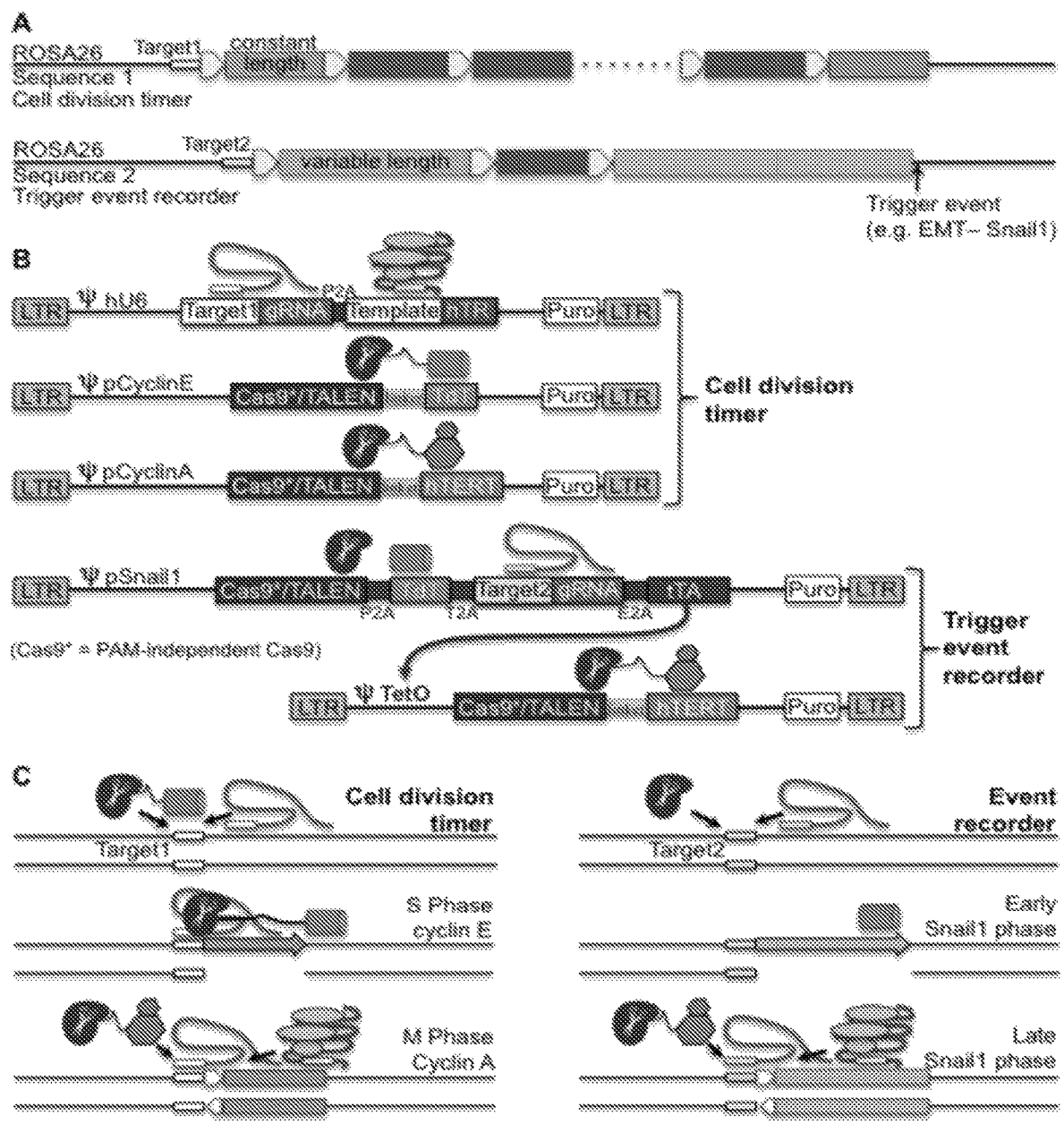
FIG. 4. An embodiment of the MCDS. (A) Diagram of recorded units of a variable barcode and a constant tag written on two different sites for two different purposes. Repeated events are recorded as concatenated units. (B) Components for Cell division timer (CDT) and Trigger event recorder (TER). CDT uses temporally spaced cyclins E and A promoters to drive the cutter (Cas9* or TALEN) fused to the writer TdT (variable barcode) or hTERT (constant tag). TER uses a temporally spaced, multi-use On/Off switch, in which SNAIL1 drives a Cas9* or TALEN-TdT-fusion construct (variable barcode). Tet-off transactivator (tTA) is co-expressed with TdT, and in the absence of dox, activates TetO to drive Cas9* or TALEN-hTERT fusion protein (constant tag). (C) Schematic of multi-function MCDS on several target sites. CDT uses a fused cutter and TdT writer to keep random barcode length constant. TER's cutter and TdT writer are not fused and therefore the length of random barcode reflects the amplitude of recorded signal (i.e. a signal barometer).
Figure 5:
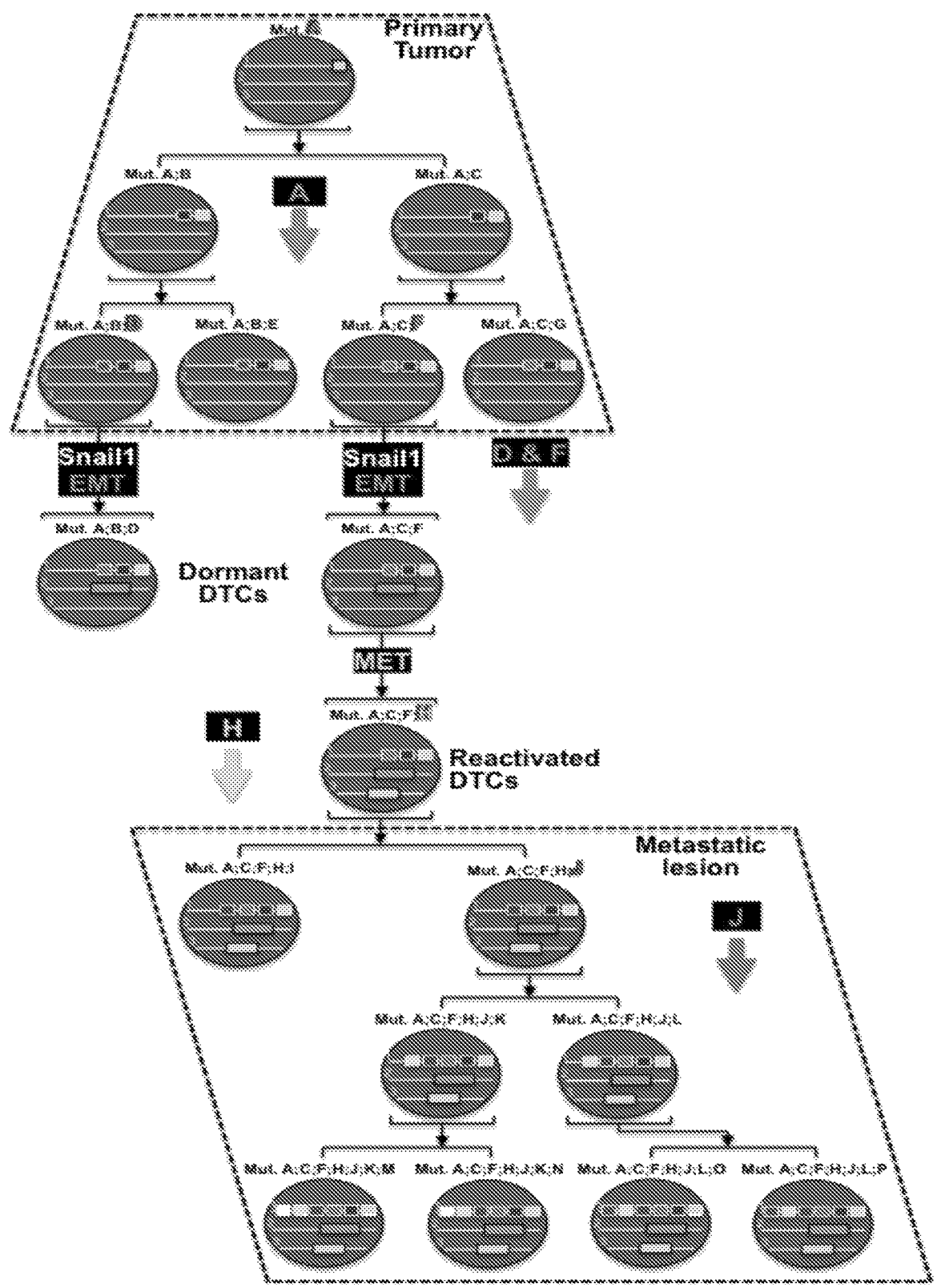
FIG. 5. A potential application of MCDS when being combined with single cells NGS and RNA seq to identify driver genetic: and epigenetic mutations during critical milestones of breast cancer progression. In this example, a detailed cellular family tree is constructed based on NGS of written random barcodes recorded on 3 separate sequences. Sequence 1 is for cell cycle counting, 2 for EMT initiation/SNAIL1 event triggered recording. 3 for MET-event triggered recording. Alignments of genetic mutations and epigenetic alternations revealed by NGS, trigger event recorder and signal barometer provide a powerful platform to identify driver changes. In this example, eGFP-labeled tumor cells are used for sorting. Mutation A is likely a driver change (depicted as colored downward arrows) for primary tumor growth; Mutations D and F for SNAIL1-dependent cancer EMT initiation; Mutation H for MET or reactivation of growth of dormant DTCs; and Mutation J for growth of metastatic tumors, respectively.
Figure 6:
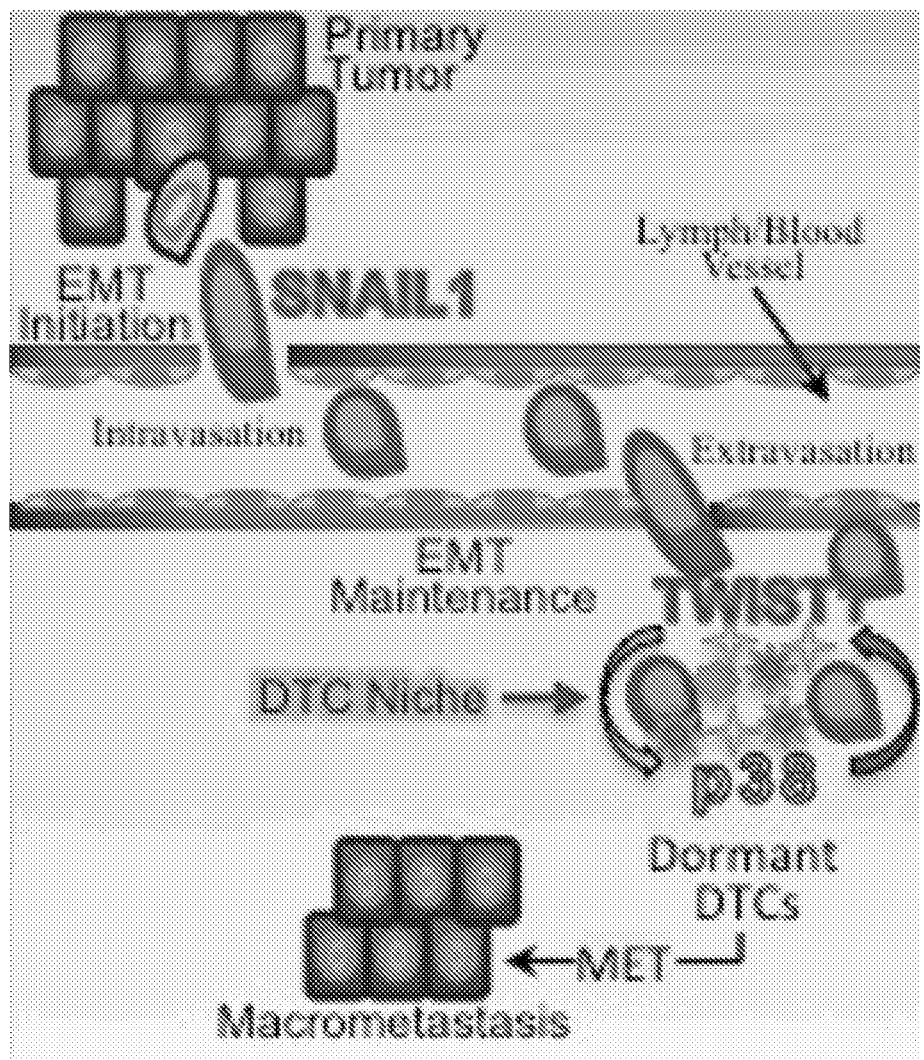
FIG. 6. The metastatic cascade.

MCDS employs parallel monitoring of individual cells in vivo and includes information on lineage tracing, biological timing, and molecular activity dynamics at the single cell level. The lineage tracing data can be used to construct comprehensive cellular family trees (FIG. 1). The biological timing data is based on a counter of cell division cycles or other biologically relevant time such as the circadian rhythm (FIG. 2). Cellular and molecular activity dynamics recording is triggered by the expression of a gene of interest or other physiologic events, e.g. fate decision or EMT initiation (FIGS. 3 and 4). Insights gleaned from this novel system provide genetic and epigenetic understanding of normal development, tissue maintenance and repair, and tumor evolution among others at the single cell level (FIG. 5).

MCDS involves recording the cellular and molecular activities triggered by a cellular event (e.g. cell division cycle) into the DNA of a cell at a predefined location as a random DNA sequence or a unique DNA barcode without (FIG. 1) or with (FIGS. 2-4) a short constant end tag to mark the beginning and end, respectively, of the event. At the next event cycles, units of random, unique barcode with or without a constant end tag are added sequentially. The random or unique DNA sequences inserted in to the genome of a cell can be later read by NGS. The DNA being modified can be the genomic DNA of the cell or extra-genomic DNA, such as, mitochondrial DNA or artificially introduced DNA.

An embodiment of the invention provides a cell comprising genes that constitutes MCDS. The cell comprises, incorporated into the cell's genome, the following constructs:
  i) a gene encoding a sequence specific nuclease (a DNA cutter) that creates a DSB in a sequence specific manner in a target double stranded DNA; and
  ii) a gene encoding a DNA polymerase (a DNA writer) which adds a DNA sequence to the DSB created by the DNA cutter, wherein, the gene encoding the DNA cutter and the gene encoding the DNA writer are under the control of a promoter which is activated by the occurrence of a cellular event of interest.

As such, the MCDS of the invention comprises two enzymes: a DNA cutter which comprises a target site recognition sequence coupled with a nuclease, and a DNA polymerase i.e., a DNA writer.

A target site recognized by the DNA cutter is selected to have one or more of the following characteristics: 1) Being constitutively accessible in many cell types so that the cutter and writer can have easy access to the locus, for example, the ROSA26 locus, the hypoxanthine phosphoribosyl transferase (Hprt), the chemokine (CC motif) receptor 5 (CCR5) gene locus; the adeno-associated virus site 1 (AAVS1); and the human orthologue of the mouse ROSA26 locus; 2) Not being present in a hypermutated region of the genome to minimize subsequent changes to the sequences written by the DNA writer.

The role of the DNA cutter is to recognize a specific location in the DNA of a cell where it will create a DSB in the DNA sequence to prepare for the writer to add nucleotides. In one embodiment, the DNA cutter is a genetically engineered nuclease. Non-limiting examples of nucleases that can be modified and used in the MCDS include the Clustered Regularly-Interspaced Short Palindromic Repeats (CRISPR) Associated Protein-9 Nuclease (Cas9), the Transcription Activator-Like Effector Nuclease (TALEN) and Zinc Finger Nuclease (ZFN).

The Cas9 cutter: Cas9 is composed of a guide RNA (gRNA or the finder) and an endonuclease. gRNA recognizes a specific target site by complementary pairing and recruits Cas9. Successful binding of wild-type Cas9 to its target sequence requires the Protospacer Adjacent Motif (PAM) NGG immediately following the target sequence. After the gRNA/Cas9 complex binds to the target sequence, Cas9 endonuclease activity creates a DSB at approximately 3-4 nucleotides upstream of PAM. As PAM is severed from its target sequence, Cas9 cannot bind efficiently to the same target in subsequent cycles. To mitigate this limitation, in one embodiment, a modified Cas9 (Cas9*) is produced that has an altered PAM specificity. In one embodiment, Cas9* represents a Cas9-related endonuclease such as Cpf1 that cuts downstream of the PAM sequence at nucleotide 18 on the forward strand and 23 on the reverse strand, thus creating a sticky end DSB so that the PAM will not be lost after being cut by this PAM-retaining Cas9*. Certain examples of Cas9* relevant to the invention are described in the Zetsche et al. (2015) reference, which is incorporated herein by reference in its entirety.

In another embodiment, a PAM-independent Cas9* is produced that does not require PAM for efficient binding and cutting (FIGS. 1-4). A PAM-independent Cas9* can be produced by replacing Cas9's nuclease domain with another endonuclease that does not require a PAM, for example, Fok1 nuclease.

TALEN or ZFN: TALEN or ZFN endonucleases do not require gRNA or PAM motif. A new DNA binding protein complex for each target sequence can be designed. TALENs are comprised of tandem, polymorphic amino acid repeats that individually recognize contiguous nucleotides in a DNA sequence. Complete TALEN cutter according to the invention is generated by fusing a TAL effector DNA-binding domain to a DNA cleavage domain such as the plant pathogenic *Xanthomonas* spp. FokI nuclease.

ZFN can also be produced by fusing FokI nuclease to Cys2His2 zinc fingers that function as specific DNA binding domain, recognizing different nucleotide triplets.

The DNA writer: The DNA writer used in the MCDS of the invention is a DNA polymerase that can add free nucleotides to an opened end of a DSB in the DNA in a template-dependent or a template-independent manner. The processivity of the writer head, i.e., the ability of a writer head indicated in terms of the length of nucleotide chain synthesized by the writer head at a DSB, is between 50 to 300 bp, about 60 to 275, about 70 to 250, about 80 to 225, about 90 to 200 or about 100-200 bp per recording cycle. Processivity higher than about 400-500 bp may be used.

Processivity of a DNA writer can be controlled by one or more of the following means: 1) selecting a low-processive enzyme or creating a low processive enzyme through site directed mutagenesis; 2) lowering the expression of the DNA writer by choosing a weaker promoter among the promoters associated with an event of interest; 3) shortening the duration of writer expression by selecting a promoter that has a narrower peak of activity during among the promoters associated with an event of interest (for example, the cyclin E promoter, which is active only briefly during the $G_1$-S transition of the cell cycle); or 4) using a delayed negative regulator of the writer to ensure that writer's activity is brief, for example, coupling a writer expression with a slightly delayed expression of a writer-specific shRNA using 2 promoters that are either temporally spaced naturally—cyclins E and A, or engineered to be temporally spaced (FIG. 4B).

An example of the gene activity modulation is the tamoxifen inducible system. The gene of interest is fused with a mutated ligand-binding domain from the oestrogen receptor (ER) gene. In the absence of the inducer, 4-hydroxytamoxifen (4-OHT), the fusion protein product is sequestered by heat-shock proteins (HSPs). Addition of 4-OHT results in the release of the fusion protein. Therefore a writer-ER fusion protein can be engineered so that written sequence length can be controlled by withdrawal of 4-OHT.

In one embodiment, the barcode length is kept unchanged at <200 bp by fusing the cutter to the writer head through a flexible linker of a predetermined length. Non-limiting examples of flexible linkers that can be used in the invention include polyG chain or repeated units of $(GGGS)_n$ or other reported flexible linkers such as KESGSVSSE-QLAQFRSLD, EGKSSGSGSESKST and $(GSAGSAAGSGEF)_n$. The cutter anchors the fusion complex at the target site as the writer head adds nucleotides until the length of the added barcode approximates that of the linker, at which time the writer stops (FIG. 9). In certain embodiments, a writer linked to a cutter is used in the MCDS designed to record a biological clock, the cell cycle or circadian rhythm. For events that are less frequent than cell cycle or circadian rhythm, the total written sequence length is unlikely to be excessive. Therefore, a linker may not be needed in such systems.

Figures 11A, 11B:
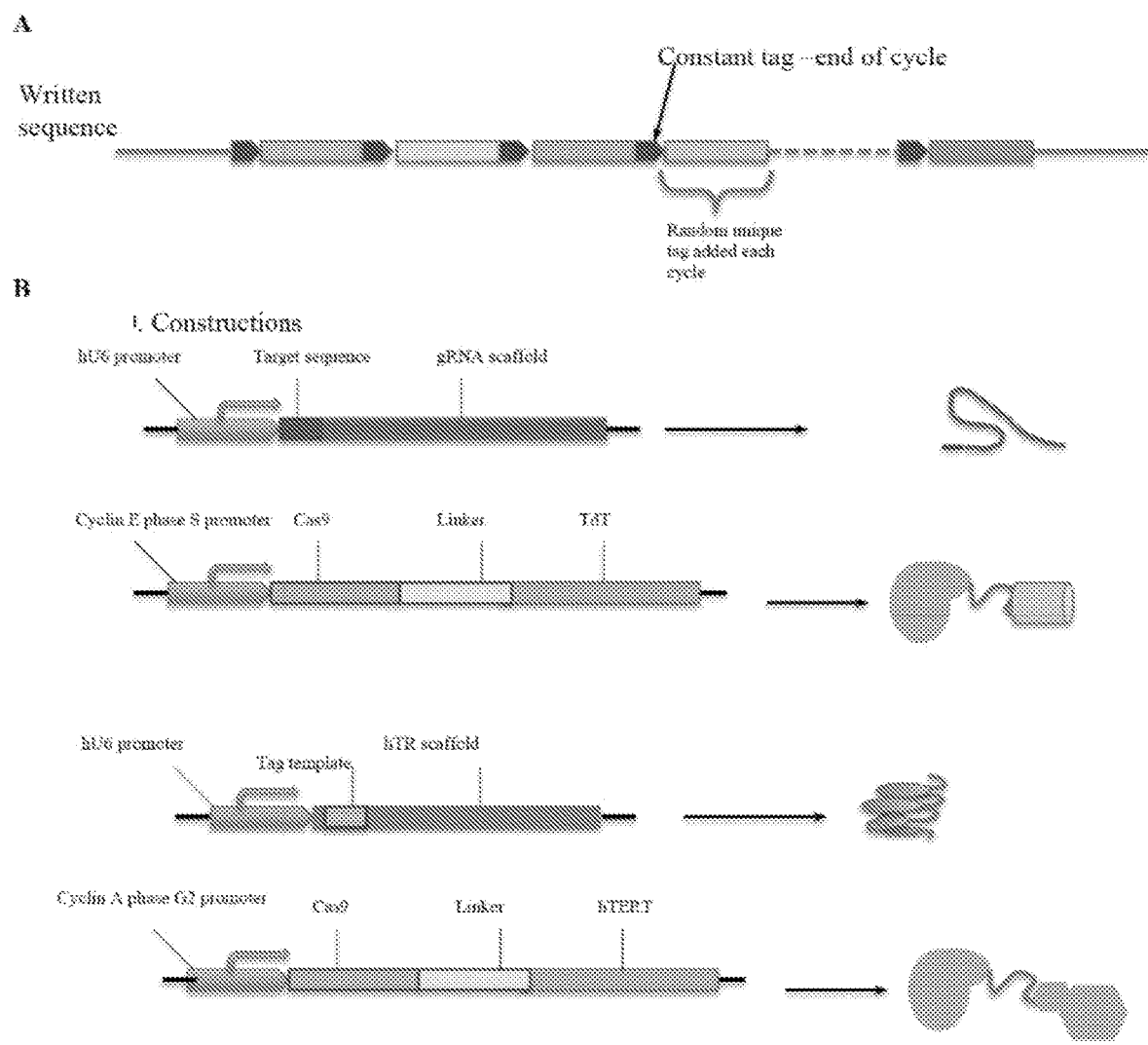
FIGS. 11A-11C and 12A-12C. Depict the construction and working scheme of written sequences in MCDSs 2A and 2B. These MCDSs are used for lineage tracing and family tree construction and for recording timing of events of interest. There are two writers in these MCDSs. At each event cycle a random, unique barcode followed by a constant end-of event tag are added by two different writers. Similar to MCDS 1, a fused DNA cutter-writer (Cas9* or TALEN-TdT) complex driven by the cyclin E promoter and coupled with a constitutively expressed gRNA (omitted if TALEN is used) will add a random, unique barcode of constant length, which is approximately the length of the flexible linker. In addition, the second DNA cutter-writer complex (Cas9* or TALEN-hTERT) driven by the cyclin A promoter ($S_1$-M transition of the cell cycle) and guided to the same target sequence by the gRNA finder (omitted if TALEN is used) will add a constant end-of-cell cycle tag using a 8bp template provided by the constitutively produced hTR (scaffold and template for telomerase). In MCDS 2B the first cutter and writer are not fused and therefore the length of the random, unique barcodes varies.
Figure 11C:
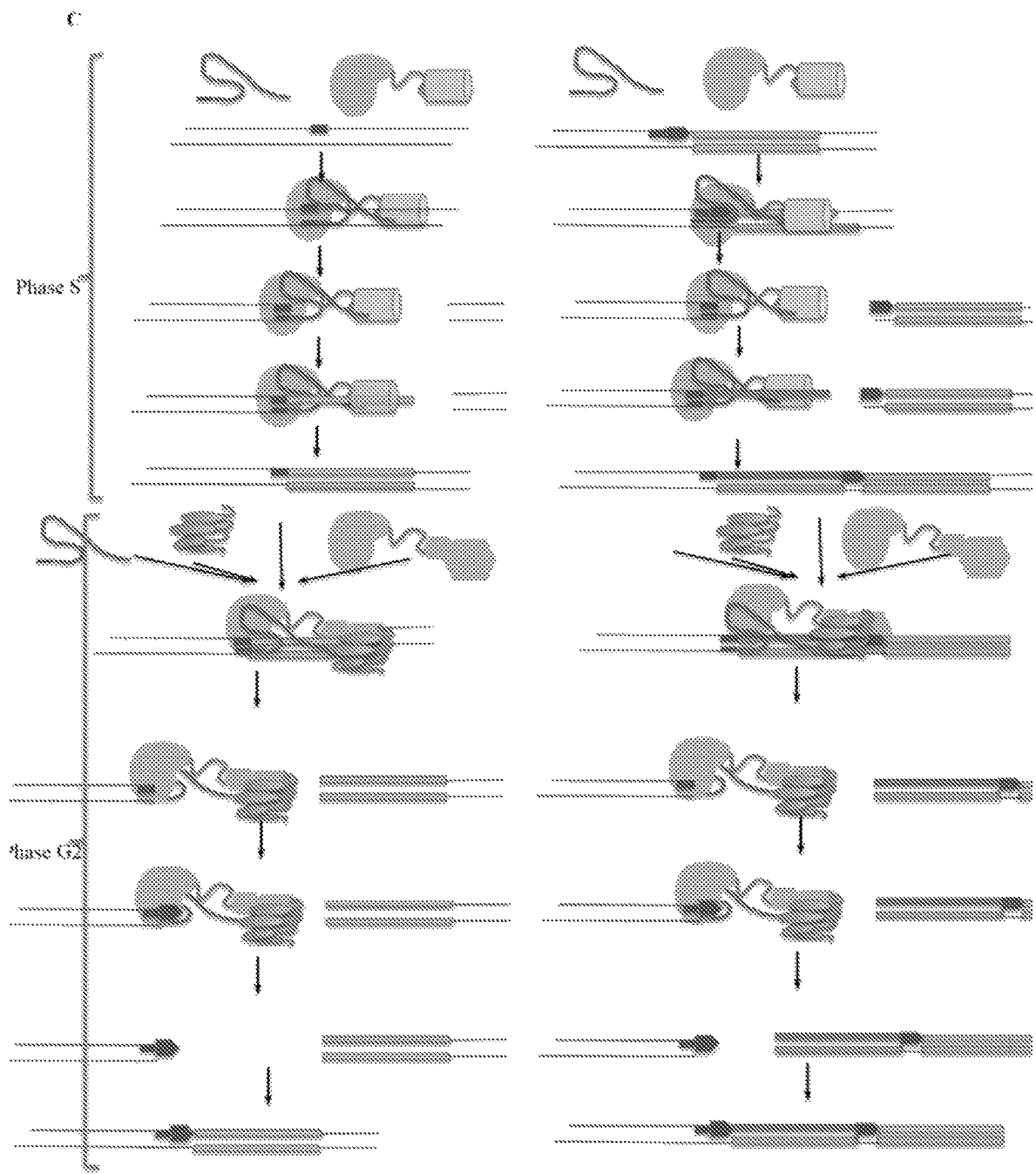
Figure 12A:
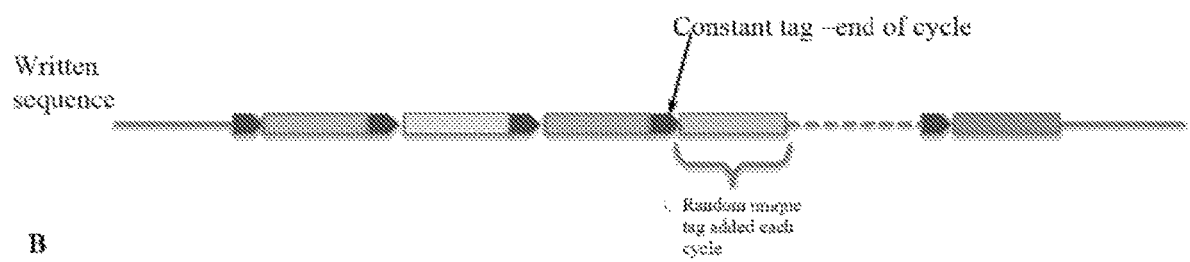
Figure 12B:
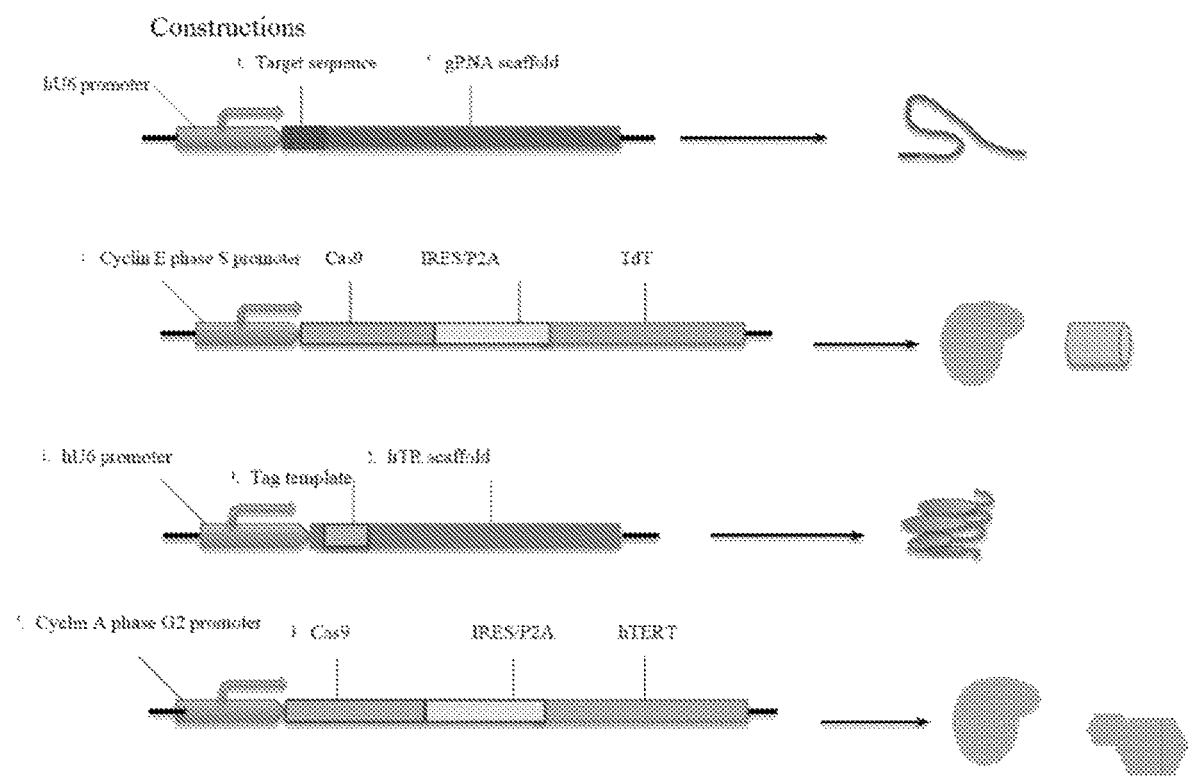
Figure 12C:
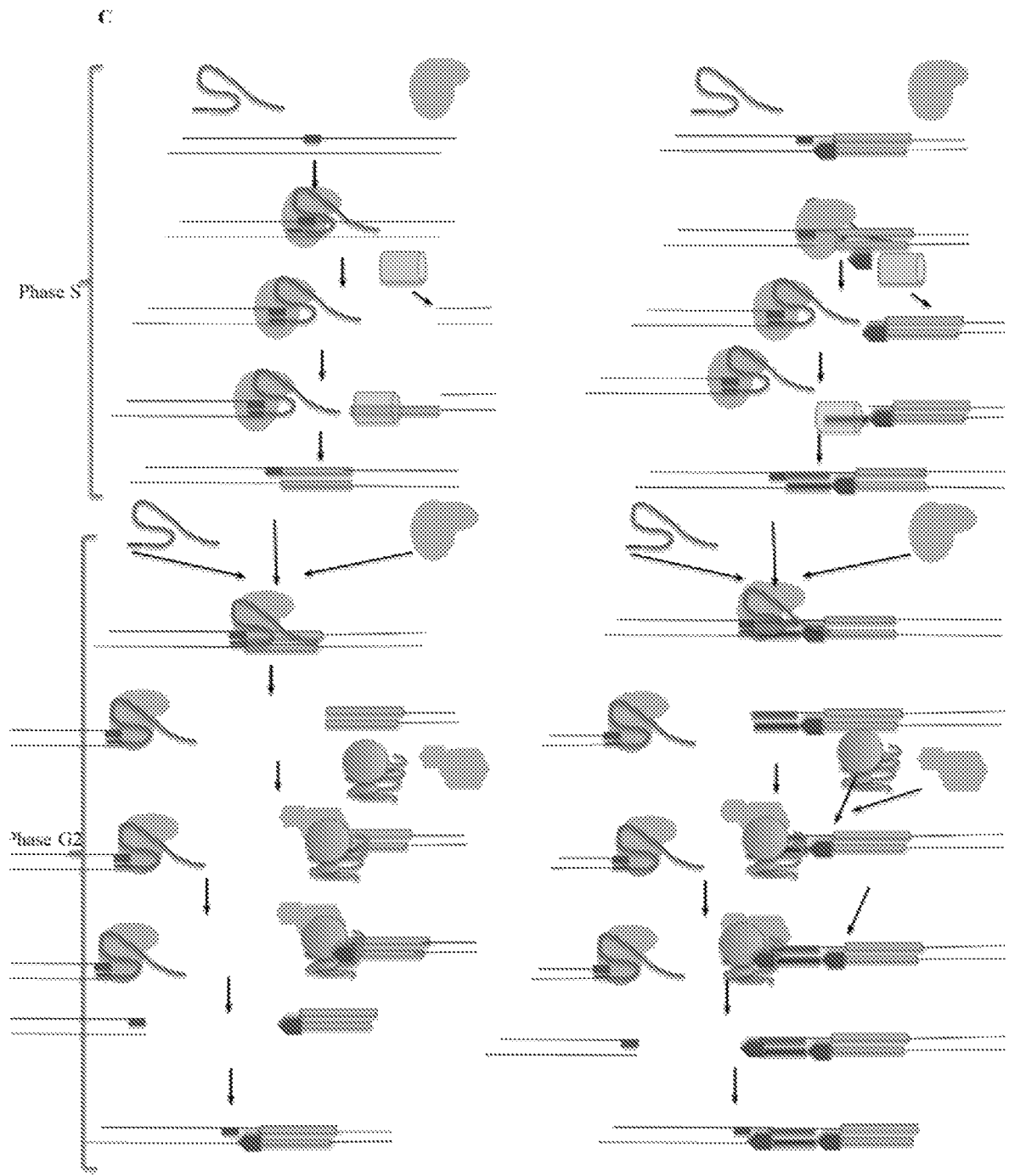

When differences in the activity dynamics of an event provide critical information, for example, the occurrence of an event and the strength of a signal are of interest, the strength of the event can be recorded as indicated by the length of the barcode written by a DNA writer. In such cases, the barcode length is regulated by the strength of the cellular signals or promoters of interest. As such, the cutter and writer are not fused (FIGS. 10-12).

The length of the unique barcode contains information on signal dynamics (i.e. magnitude, frequency and duration) associated with the molecular event of interest (e.g. promoter activity of a gene of interest), while their sequence identity uniquely discriminates between individual cells. By comparing the number and sequence identity of unique barcodes between different cells, a cellular family tree can be retroactively constructed (FIG. 1A and 1D). On the other hand, cellular or molecular activity history can be reconstructed using the number and length of unique barcodes of the event recorder in relation to a reference biological clock (e.g. cell division or circadian cycle) so that the timing and duration of the event of interest can be ascertained (FIG. 2).

Template-independent writers in MCDS: Template-independent writers used in the MCDS introduce sequences of infinite variations to store information on unlimited numbers of cellular events.

An example of polymerases that can be used as a template-independent DNA writer is Terminal deoxynucleotidyl Transferase (TdT), which adds random, unique sequences to opened DNA ends in a DSB. TdT does not require a template strand. TdT can write nucleotides at a 3' overhang, blunt or 3' recessed DNA ends. Non-limiting examples of a template-independent DNA writer that can synthesize blunt-end addition reaction include DNA polymerase alpha from chick embryo, rat DNA polymerase beta, reverse transcriptase from avian myeloblastosis virus, and DNA polymerase I from *S. cerevisiae*. Additional examples of template-independent writers suitable for use in the MCDS of the invention are well known to a person of ordinary skill in the art and such embodiments are within the purview of the invention.

Template-dependent writers in MCDS: In certain embodiments, a template-dependent DNA polymerase is used as a DNA writer in the MCDS of the invention. Template-dependent DNA writer is used, particularly, to mark the end of cellular events to provide greater timing resolution to the recorded history. A template-dependent DNA writer adds constant, predefined sequences and requires a template. The template can be an RNA. When the template is RNA, the template does not interfere with the DNA sequence to be written. A template-dependent DNA writer provides reverse transcriptases (RT) activity. An example of template-dependent writer is telomerase, which is a ribonucleoprotein polymerase that catalyzes the extension of telomeric DNA in eukaryotes with a tandem repeat of a constant sequence ("TTAGGG" in humans), using a single-stranded RNA molecule hTR as a template. Additional examples of the template-dependent DNA writer include reverse transcriptases encoded in Drosophila retrotransposable elements or retrotransposons, and retroviral reverse-transcriptase that specifically add constant DNA stretches to chromosome ends. In certain embodiments, a template-dependent writer, for example, reverse transcriptases encoded in Drosophila retrotransposable elements or retrotransposons, and retroviral reverse-transcriptase is engineered to reduce its processivity.

The human telomerase complex is composed of human telomerase reverse transcriptase (hTERT), a RNA template (TERC or TR) and accessory proteins such as dyskerin, NOP10, NHP2, and GAR1. Telomerase activity can be reconstituted in a cell free system.

In Drosophila, telomere repeats are two retrotransposable elements, HeT-A and TART. Uniquely in *Drosophila melanogaster*, a third retrotransposable element known as TAHRE is also present and composed of an element combining sequences of Het-A and TART. These retrotransposons specifically transpose to chromosome ends. The length of Drosophila telomere repeats are, however, too long (e.g. >6 kb) to be useful to serve as a constant tag in the MCDS of the invention. The same excessive length constraints (usually in kb range) also limit the usefulness of other enzymes that add constant DNA stretches such as reverse transcriptase encoded in retrostransposons and retroviral reverse transcriptase. Therefore an engineered version of retroviral reverse transcriptase with reduced processivity can be produced to serve as alternative to human telomerase as a constant tag DNA writer for this invention.

In one embodiment, the gene encoding the DNA cutter and the gene encoding the DNA writer are both under the control of the same copy of the promoter, i.e., the two genes are both downstream of the same copy of the promoter and are controlled by the same copy of the promoter. In another embodiment, the gene encoding the DNA cutter and the gene encoding the DNA writer are under the control of different copies of the promoter, the gene encoding the DNA cutter and the gene encoding the DNA writer are under the control of separate but identical or equivalent promoter. Equivalent promoters may not have the same DNA sequence; however, the activities of two equivalent promoters are under the control of the same regulatory biomolecules.

The regulatory promoters: The regulatory promoters of MCDS are promoters that regulate the timing, duration and amplitude of the expression of the DNA cutters and DNA writers in the response to a various cellular event of interest. Examples of cellular timing elements are time oscillating clock signals. Naturally occurring clock signals include the cell division cycle (FIGS. 1, 2 and 4), the circadian rhythm (FIG. 3), the segmentation clock, and the p53 and calcium ion ($Ca^{++}$) oscillators. The oscillatory frequency and amplitude can therefore be tunable to fit the needs of different MCDS versions. The amplitude regulators are promoters that vary their activity according to the triggering signal's strength. For example, SNAIL1 promoter activity depends on the duration and concentration of the EMT-inducing factor (e.g., TGFβ1). Therefore, a combination of a DNA cutter and a DNA writer under the control of the SNAIL1 promoter will be expressed based the duration and concentration of the EMT-inducing factor. The level of the expression of a DNA writer affects the barcode lengths. Therefore, higher concentration and/or duration of EMT-inducing factor would lead to longer barcode length and lower concentration and/or duration of EMT-inducing factor would lead to shorter barcode length.

The duration and amplitude regulator is gene promoters that vary the degree and extent of their activity in response to the strength of cellular signals, e.g. positive or negative feedback or feed forward loops in cellular signal transduction, ionic concentration (e.g. $Ca^{++}$, pH) and temperature. A special kind of cellular timing element is time oscillating signals. These signals can be naturally produced or artificially introduced. They can serve in this invention as a biological timer or clock. Some examples of naturally occurring clock signals are the oscillatory dynamics of cyclin-dependent kinases driving the cell cycle, circadian rhythm, the segmentation clock, oscillation in p53 and NF-κB expression, and $Ca^{++}$ ion oscillation. The frequency and amplitude of oscillation can be tuned.

In certain embodiment, the cellular event of interest is selected from: an initiation of a cell cycle, a termination of the cell cycle, an initiation of epithelial to mesenchymal transition (EMT), an initiation of mesenchymal to epithelial transition (MET), circadian rhythm, activation of cellular invasion, initiation of an immune reaction, neuronal excitation or a transformation to a cancerous state. Additional events of interests that can be monitored or tracked using the MCDS of the invention are well known to a person of ordinary skill in the art and are apparent to a person of ordinary skill in the art. Such embodiments are within the purview of the invention.

An embodiment of the MCDS of the invention contains more than one, for example, two, three, four or five pairs of DNA cutters and DNA writers. In an embodiment, each of the plurality of pairs of DNA cutters and DNA writers differ from each other in certain aspects of MCDS. For example, the promoters controlling different cutter/writer pairs can be different or the cutter/writer activity can be different. A person of ordinary skill in the art can design versions of MCDS where more than one pairs of DNA cutter/writer are present and each of the pairs modify the target DNA in a unique manner so that the history of events of interest occurred in the cell can be deciphered based on distinguishable writer activity.

An embodiment of the invention provides MCDS comprising two pairs of DNA cutter/writer. The cell comprises, incorporated into the cell's genome, the following constructs:

i) a gene encoding a first sequence specific nuclease (a first DNA cutter) that creates a first DSB in a first sequence specific manner in a first target double stranded DNA, and a gene encoding a second sequence specific nuclease (a second DNA cutter) that creates a second DSB in a second sequence specific manner in a second target double stranded DNA; and ii) a gene encoding a first DNA polymerase (a first DNA writer) which adds a first DNA sequence to the first DSB created by the first DNA cutter, and a gene encoding a second DNA polymerase (a second DNA writer) which adds a second DNA sequence to the second DSB created by the second DNA cutter, wherein, the genes encoding the first DNA cutter and the first DNA writer are under the control of a first promoter which is activated by the occurrence of a first cellular event of interest and the genes encoding the second DNA cutter and the second DNA writer are under the control of a second promoter which is activated by the occurrence of a second cellular event of interest.

In certain embodiments, the first and the second DNA cutters are selected from a PAM-independent Cas9*, PAM-retaining nuclease Cpf1, or TALEN capable of recognizing ROSA26-located target, zinc finger nuclease, and wherein the first and the second DNA cutters are different from each other; whereas, in certain other embodiments, the first and the second DNA cutters are selected from a PAM-independent Cas9*, PAM-retaining nuclease, or TALEN capable of recognizing ROSA26-located target, zinc finger nuclease, and wherein the first and the second DNA cutters are same.

In a further embodiment, the first and the second DNA writers are different from each other. For example, the first DNA writer is a template-independent DNA polymerase and the second DNA writer is a template-dependent DNA polymerase and vice versa. Accordingly, if the first DNA writer is template-independent, the second writer is template-dependent and if the first DNA writer is template-dependent, the second writer is template-independent.

Various aspects of DNA cutters and DNA writers described above are also applicable to the embodiments of the invention where more than one pair of DNA cutters/writers are used.

In one embodiment, the gene encoding the first DNA cutter and the gene encoding the first DNA writer are both under the control of the same copy of the first promoter; whereas, in certain embodiments, the gene encoding the second DNA cutter and the gene encoding the second DNA writer are both under the control of the same copy of the second promoter.

In a further embodiment, the gene encoding the first DNA cutter and the gene encoding the first DNA writer are both under the control separate but identical or equivalent first promoters; whereas, in an even further embodiment, the gene encoding the second DNA cutter and the gene encoding the second DNA writer are both under the control of separate but identical or equivalent second promoters.

A person of ordinary skill in the art can appreciate that any combination of same or separate but identical or equivalent promoters for various pairs of DNA cutters and writers can be designed and such embodiments are within the purview of the invention.

In an embodiment of the MCDS, an On/Off switch is used. Certain examples of On/Off switch are described below:

Single-use On/Off switch: A single-use On/Off switch can be constructed using recombinase systems like Cre-loxP and Flp-FRT, and ΦC31. For example, the expression of gRNA and hTR can be regulated by positioning a pair of loxP sites at strategic locations. For example, in an example of the "On switch", a cassette containing a polyA stop signal flanked by 2 loxP sites (LSL) is inserted in the hU6 promoter region. When the recombinase Cre is expressed in response to the EMT initiation, the LSL cassette is excised, thereby permanently turning on the expression of the DNA cutter (FIG. 3). For the Off switch, the entire DNA cutter gene is flanked by 2 loxP sites allowing the gene to be permanently inactivated by Cre.

In one embodiment, the DNA cutter and the DNA writer is separately driven, for example, by a SNAIL1-independent constant timing oscillator like the circadian rhythm. In this embodiment, the timing of EMT initiation is captured either as the commencement (On switch) or interruption (Off switch) of barcode addition in reference to the circadian rhythm.

Multi-use On/Off switches: Multi-use On/Off switches are constructed by using the event-specific promoters that closely mirror the profile of the recorded event and are temporally spaced so that the constant end tag is not added until the random barcode writing has completed. In one example, promoters for cyclins E and cyclin A are used for recording the $G_1/S$ and $S/G_2$ phases of the cell cycle, respectively. In another embodiment, the event-specific promoters that closely mirror the profile of the recorded event and are engineered to be temporally spaced so that the activation of the second promoter is dependent on completion of the first event/promoter. For example, the expression of a first DNA cutter, a first DNA writer and the tet-off transactivator (tTA) is linked in response to the EMT initiation, for example, SNAIL1. The second DNA cutter and the second DNA writer are not expressed until tTA activates the TetO promoter in the absence of doxycycline (FIG. 4). Thus, a time delay is introduced between the two combinations of the DNA cutters and the DNA writers.

In another embodiment of the multi-use On/Off switch, the first writer is a random barcode writer, such as TdT, which reflects the duration and amplitude of the SNAIL1 promoter activity; whereas, the second writer is a template-dependent DNA writer, for example, telomerase, which marks the end of the event with a constant tag. In a further embodiment, an shRNA specific for the first writer is added to the second writer construct so that when the second writer construct is expressed, the expression of the first writer is inhibited. As such, the constant end tag writing marks the end of the first event recording.

MCDS is used to determine the history of cellular events in a cell comprising the MCDS. According, an embodiment of the invention provides, a method comprising the steps of:
  i) culturing a cell comprising MCDS of the invention,
  ii) isolating genomic from the cell,
  iii) obtaining the genomic sequence of the cell or obtaining the sequence of the region within the genomic DNA of the cell around the sites recognized by the DNA cutters,
  iv) based on the sequences obtained in step iii), determining the occurrence of the number and sequence of the events of interest that occurred in the cell during culture.

The methods of culturing cells, isolating genomic DNA of a cell, and sequencing the genomic DNA or sequencing certain regions of interest within the genomic DNA of a cell are well known to a person of ordinary skill in the art and such embodiments are within the purview of the invention. For example, a single cell based NGS can be used to sequence the genome of a cell.

In one embodiment, the target region of the genomic DNA which contains the target sites for the cutter is under a promoter. Therefore, an mRNA is synthesized from target region. The mRNA will contain and amplify the sequences written by the DNA writer. In this case, RNA sequencing will be used instead of DNA sequencing for reading the written sequences.

A further embodiment of the invention provides nucleotide constructs containing the genes encoding combinations of DNA cutters and DNA writers under the control of appropriate promoters. The DNA construct can be placed in appropriate vehicles for transformation of a cell, for example, viral vectors, plasmids, and linearized naked DNA. Additional examples of DNA constructs appropriate for the transformation of cells are well known to a person of ordinary skill in the art and such embodiments are within the purview of the invention.

Viral vectors (retroviral or lentiviral) carrying constructs can be used to transduce target cells. Alternatively the CRISPR/Cas9 technology can be used to knock-in the constructs into the genome. For in vivo applications, the constructs can be introduced into the tissue of interest by direct injection of viral vectors carrying the constructs. Alternatively, cell lines carrying the constructs can be produced ex vivo and transplanted into an in vivo model.

The constructs providing MCDS can be present in a single construct or more than one constructs. For example, genes encoding DNA cutter and writer can be either on the same nucleotide but under the control of different promoters or under one promoter driving expression of different proteins. The genes can be separated by secondary ribosomal recognition site such as IRES, P2A or RNA nuclease CRISPR based (Csy4). Csy4 recognizes 26 bp RNA sequence and cut inside the synthesized mRNA sequence.

Accordingly, an embodiment of the invention provides a nucleotide comprising:
  i) a gene encoding a sequence specific nuclease (a DNA cutter) that creates a DSB in a sequence specific manner in a target double stranded DNA; and
  ii) a gene encoding a DNA polymerase (a DNA writer) which adds a DNA sequence to the DSB created by the DNA cutter,
wherein, the gene encoding the DNA cutter and the gene encoding the DNA writer are under the control of a promoter which is activated by the occurrence of a cellular event of interest.

A further embodiment of the invention provides a nucleotide comprising:
  i) a gene encoding a first sequence specific nuclease (a first DNA cutter) that creates a first DSB in a first sequence specific manner in a first target double stranded DNA, and a gene encoding a second sequence specific nuclease (a second DNA cutter) that creates a second DSB in a second sequence specific manner in a second target double stranded DNA; and
  ii) a gene encoding a first DNA polymerase (a first DNA writer) which adds a first DNA sequence to the first DSB created by the first DNA cutter, and a gene encoding a second DNA polymerase (a second DNA writer) which adds a second DNA sequence to the second DSB created by the second DNA cutter,
wherein, the genes encoding the first DNA cutter and the first DNA writer are under the control of a first promoter which is activated by the occurrence of a first cellular event of interest and the genes encoding the second DNA cutter and the second DNA writer are under the control of a second promoter which is activated by the occurrence of a second cellular event of interest.

The nucleotide of the invention can be incorporated into the genomic DNA of an animal to produce a genetically modified animal carrying MCDS. The genetically engineered animal carrying the MCDS allows interrogation of cellular history and functions in many tissues independently or concurrently. For example, specific cell of interest can be isolated from the genetically modified animal carrying MCDS and studied according to the methods of the invention to identify biological events that occurred in the history of the cell.

In an embodiment of the invention, a nucleotide carrying MCDS is introduced into a tissue, for example, a tumor or a cancerous tissue of an animal. Once introduced into the tissue of an animal, the nucleotide can transform at least some cells from the tissue. These cells can be isolated from the animal at a later time and studied according to the methods of the invention to identify biological events that occurred in the history of the cell.

Accordingly, an embodiment of the invention provides a method comprising the steps of:
  i) introducing a nucleotide comprising MCDS of the invention, into a tissue of an animal,
  ii) a period of time after the introduction of step i), obtaining a cell from the tissue of the animal,
  iii) obtaining the genomic sequence of the cell or obtaining the sequence of the region within the genomic DNA of the cell around the sites recognized by the DNA cutters, v) based on the sequences obtained in step iii), determining the occurrence of the number and sequence of the events of interest that occurred in the cell during the period of time.

Figure 8:
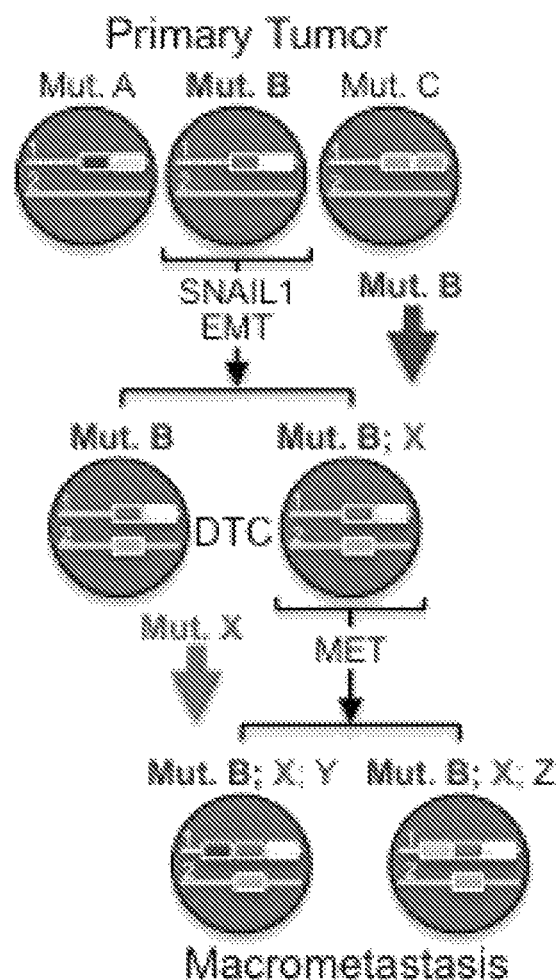
FIG. 8. A potential application of MCDS combining with NGS and RNAseq to identify driver mutations during critical milestones of breast cancer progression. In this example, mutations B and X are likely drivers of EMT/dormancy and MET, respectively. eGFP-labeled tumor cells are used for tracking.

MCDS has numerous practical applications. In one embodiment, MCDS is combined with the single-cell NGS and RNAseq to reveal a comprehensive cell division and mutational history of a cell, for example, a DTC, in temporal relation to critical events such as EMT initiation, dormancy and MET. This information provides key somatic alternations driving these transitions (FIG. 8). Thus MCDS is a powerful platform for discovery research for many research fields, for example, DTC biology, cancer research and normal cellular and developmental biology.

A further embodiment of the invention provides a method of using MCDS to mark tumor cells in a subject, for example, human, prior to surgical resection of the tumor. Tumor cells in a subject can be marked by the MCDS by intra-tumoral injection of viruses carrying MCDS. The viruses can infect and transfer the MCDS carrying genetic material into the cells of the tumor. MCDS is then present in at least some cells of the tumor and these cells can be subsequently isolated and analyzed.

For example, barcode sequences in the cells obtained from the tumor can be amplified from genomic DNA and total RNA isolated from DTCs and primary tumor, and subjected to NGS. This method can be used to detect not only rare DTCs but also their mutational burden compared to the primary tumor. Potential genetic and epigenetic drivers may then become evident and prove useful for personalized therapy.

Similar applications can also be employed for organ fate determination in a subject by administering MCDS to mark the cells in the organ. For example, cells in an organ can be marked by the MCDS by the injection of viruses carrying MCDS into the organ. The viruses can infect and transfer the MCDS carrying genetic material into the cells of the organ. MCDS is then present in at least some cells of the organ and these cells can be subsequently isolated and analyzed. The cellular map of an organ can be determined to identify important cell fate decisions that are organ specific, and that are amenable for therapeutic and tissue engineering applications.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Representative Examples of the Mcds

An example of the MCDS of the invention is described in FIG. 2. Cas9 recognizes and cleaves DNA at a predefined genomic target, namely the ROSA26 locus, using a guiding RNA (gRNA). Cas9 requires PAM sequence (NGG) upstream of the target sequence, which limits the use of Cas9 in repeated cleavages at the same site. Therefore a PAM-independent Cas9 (Cas9*) is generated by substituting the PAM-dependent nuclease subunit of Cas9 with a non-specific nuclease. Alternatively, Cas9* can be a Cas9-related endonuclease such as Cpf1 that cuts downstream of the PAM sequence at nucleotide 18 on the forward strand and 23 on the reverse strand, thus creating a sticky end DSB, can be used (this version of Cas9* is referred to as PAM-retaining Cas9* or nuclease).

In an embodiment TALEN is used, which performs the same function of Cas9*. For example, TALEN is produced by engineering TALEN to recognize a ROSA26-located target, and fused with a nuclease to create a DSB at the target.

Expression of Cas9* or TALEN (DNA cutter) is controlled by a promoter specific for a cellular event, for example, cyclins for cell cycle or SNAIL1 for EMT. At the 3' end of each Cas9* or TALEN-created DSB, a variable DNA barcode or a constant DNA tag is inserted by a DNA writer, which is co-expressed with the DNA cutter. Non-limiting examples of DNA writers include, TdT or telomerase.

Figure 7:
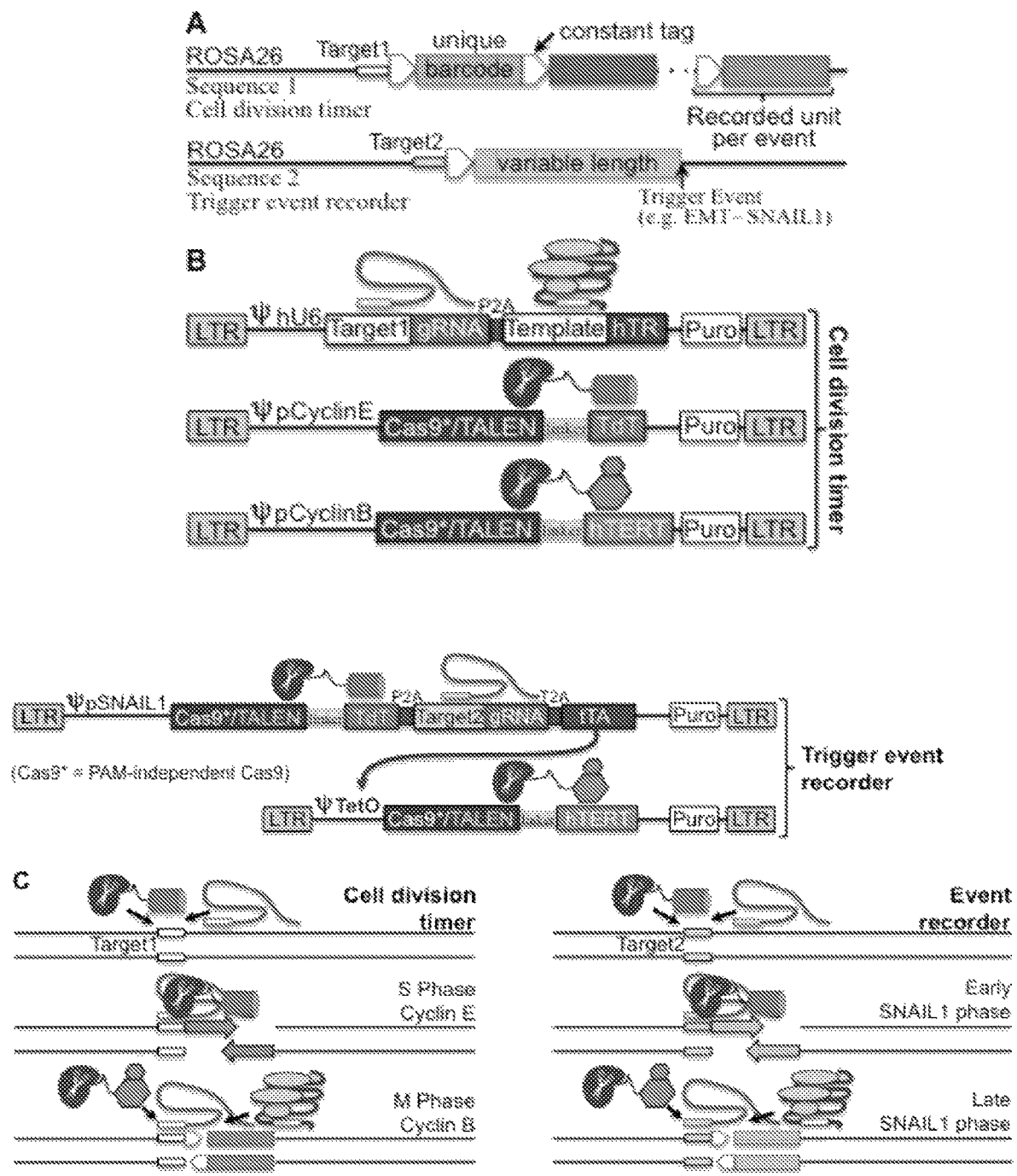
FIG. 7. Molecular Cell Diary System (MCDS). (A) Diagram of recorded units of a variable barcode and a constant tag written on 2 different sites for 2 different purposes. Repeated events are recorded as concatenated units. (B) Viral constructs of MCDS components for a Cell division timer (CDT) and Trigger event recorder (TER). CDT uses temporally spaced cyclin E and cyclin B promoters driving Cas9* or TALEN fused to either TdT (variable barcode) or hTER (constant tag). TER uses a temporally spaced system, in which pSNAIL drives the Cas9* or TALEN-TdT fusion construct (variable barcode). Tet-off transactivator (tTA) is coexpressed by pSNAIL-1 and in the absence of dox, activates a TetO promoter driving Cas9* or TALEN-hTERT fusion protein (constant tag). (C) Schematic drawing of MCDS components on target DNA sites.

To build a cellular clock or an event recorder, insertion of the variable barcode and constant tag is temporally spaced to mark the beginning and end of an event, respectively. To this end, the event-specific promoters are selected that are temporally spaced. For example, to record a cell division or an event within the cell division, promoters for proteins that are specific for the cell division event are selected. As one example, cyclin E promoter is selected to record the G0/S phase and cyclin B promoter is selected form for the M/cytokinesis phase of the cell cycle. To record an event based on a particular protein, for example, to record a SNAIL1-based event, SNAIL1 promoter is selected (FIG. 7B-C).

Once appropriate promoters are selected, a cell is modified to express one or more DNA cutters and one or more DNA writers under the control of the selected promoters. Accordingly, once the event of interest occurs in a cell, DNA writers and cutters are co-expressed with the proteins that elicit the event of interest. The expressed DNA writers and cutters modify the genomic DNA at specific locations, for example, by breaking the genomic DNA at specific locations and adding DNA sequences to the cleavage sites.

In a further embodiment, different recorded sequences are aligned using an internal timer, for example, the cell division or circadian rhythm, as a reference against which other sequences are compared to determine the timing of an event.

Additional versions of MCDS, hereinafter named, MCDS 1-5 are described.

Figures 9A, 9B, 9C:
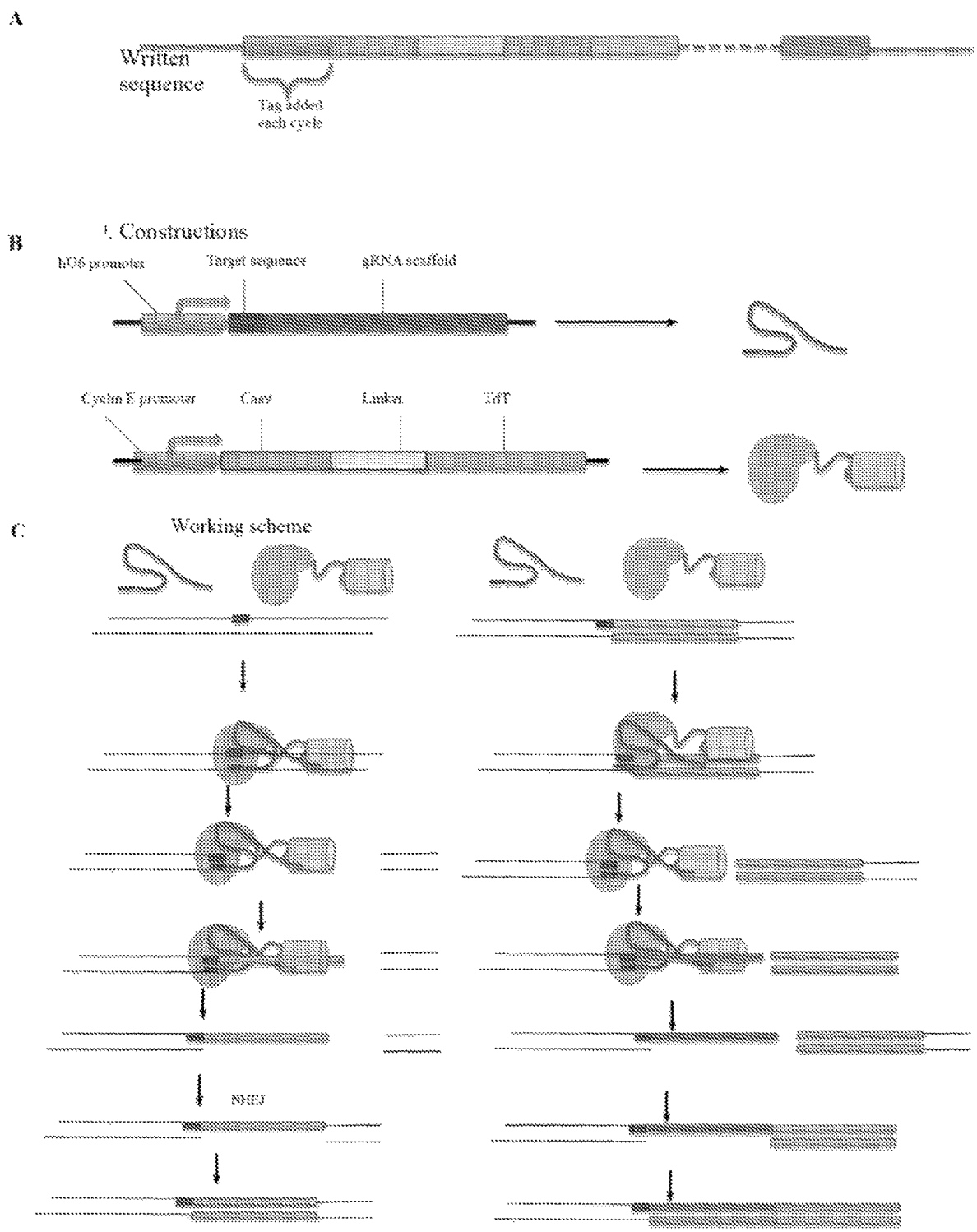
FIGS. 9A-9C and 10A-10C. Depict the construction and working scheme of written sequences in MCDS 1A and 1B. These MCDSs are used mainly for lineage tracing purposes. Only one recorder is included that incorporates a random, unique barcode at each event of the same size (approximately the length of the flexible linker, MCDS 1A) or varying size (MCDS 1B). There is no end of event tag. The finder (gRNA) is under the control of the constitutively active hU6 promoter. The DNA cutter (Cas9* or TALEN) and the DNA writer (TdT) are fused together by a flexible linker and under the control of cyclin E promoter. During the $G_1$-S transition of the cell cycle when the cyclin E promoter is activated, the DNA cutter-writer fusion complex is expressed. The constitutively expressed finder binds to a target sequence and recruits the cutter-writer complex. If TALEN is used, the finder is not necessary. A DSB is made in the DNA and the writer begins incorporating a single strand of nucleotides at random to the 3' end of the break. The length of the barcode is approximately the same length as the flexible linker. Then the cell's own DNA repair system synthesizes the complementary strand and ligates the break. MCDS 1B differs from MCDS 1A in that in MCDS 1B the cutter and writer are not fused and therefore the length of the random, unique barcodes varies.
Figures 10A, 10B, 10C:
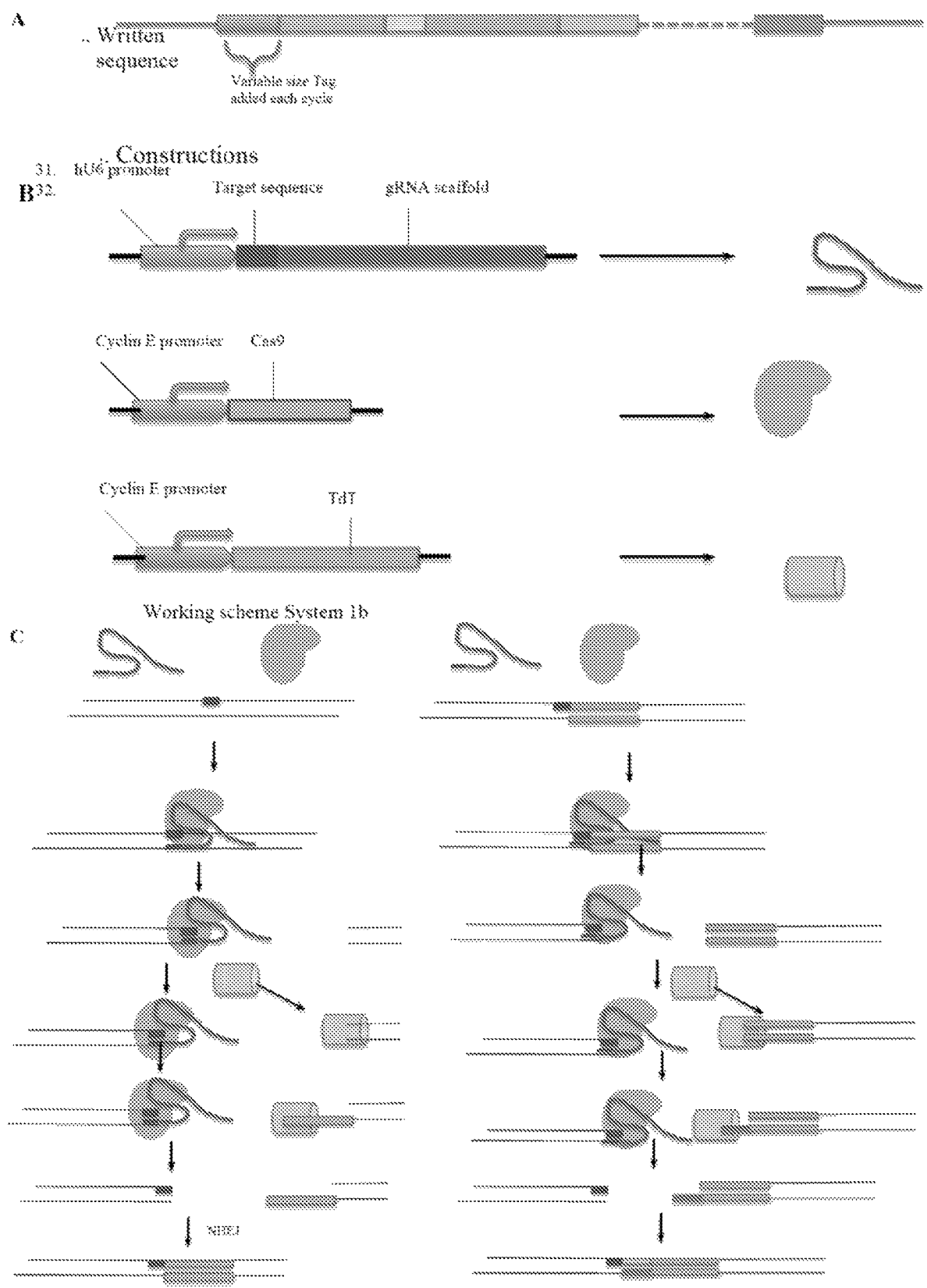

MCDS 1 is composed of unique random barcodes sequentially added with each event occurrence (FIGS. 9A and 10A). These concatenated barcodes are of either approximately the same size (MCDS 1A, FIG. 9A) or varying sizes (MCDS 1B, FIG. 10A). MCDS 1 does not have an end of event tag. This MCDS can be used for lineage tracing as the event timing and counting in individual cells cannot be resolved without end-of-event tags without using other cells as references.

MCDS 2 (FIGS. 11A and 12A): In this MCDS, the recorded sequence is composed of concatenated random unique barcodes punctuated by end-of-event constant tags between these barcodes. At the onset of each recorded event, a random unique barcode of one size (FIG. 11A) or varying sizes (FIG. 12A) is added, followed an end-of-event tag of a constant size and sequence identity (heretofore referred to as constant tag). This system can be used for lineage tracing and family tree construction and accurate biological timing of events. The recording unit (heretofore referred to as recording unit) of a random unique barcode followed by a constant tag is repeated n times, which equal the number of events. For example, if the event is cell division cycle, then the number of recording units will be generally no more than 15 to 50 times, i.e. the average numbers of cell division cycles for normal and transformed cells during their lifetime, respectively. The size of the constant tag should be long enough to minimize chance occurrence of such tag within the entire length of a recorded sequence. A length of 8 bp should be the minimum. An 8-bp sequence occurs by chance every $4^8=65536$ bp, a stretch long enough to cover more than 600 recording units of 100-bp unique barcode plus 8-bp constant tag without a high probability of a sequence identical to the constant tag occurring once by chance. The sequence of a 12-bp constant tag can occur by chance every $10^6$ bp, far exceeding the range of recording length necessary for this invention. Although increasing the length of the constant tag will decrease the chance that the tag sequence occurs by chance within a defined sequence length, it will also increase the overall sequence length that needs to be PCR-amplified and subsequently sequenced, and thus decreasing PCR amplification efficiency and/or increasing NGS bp read, cost and time (see below), respectively.

Figure 13:
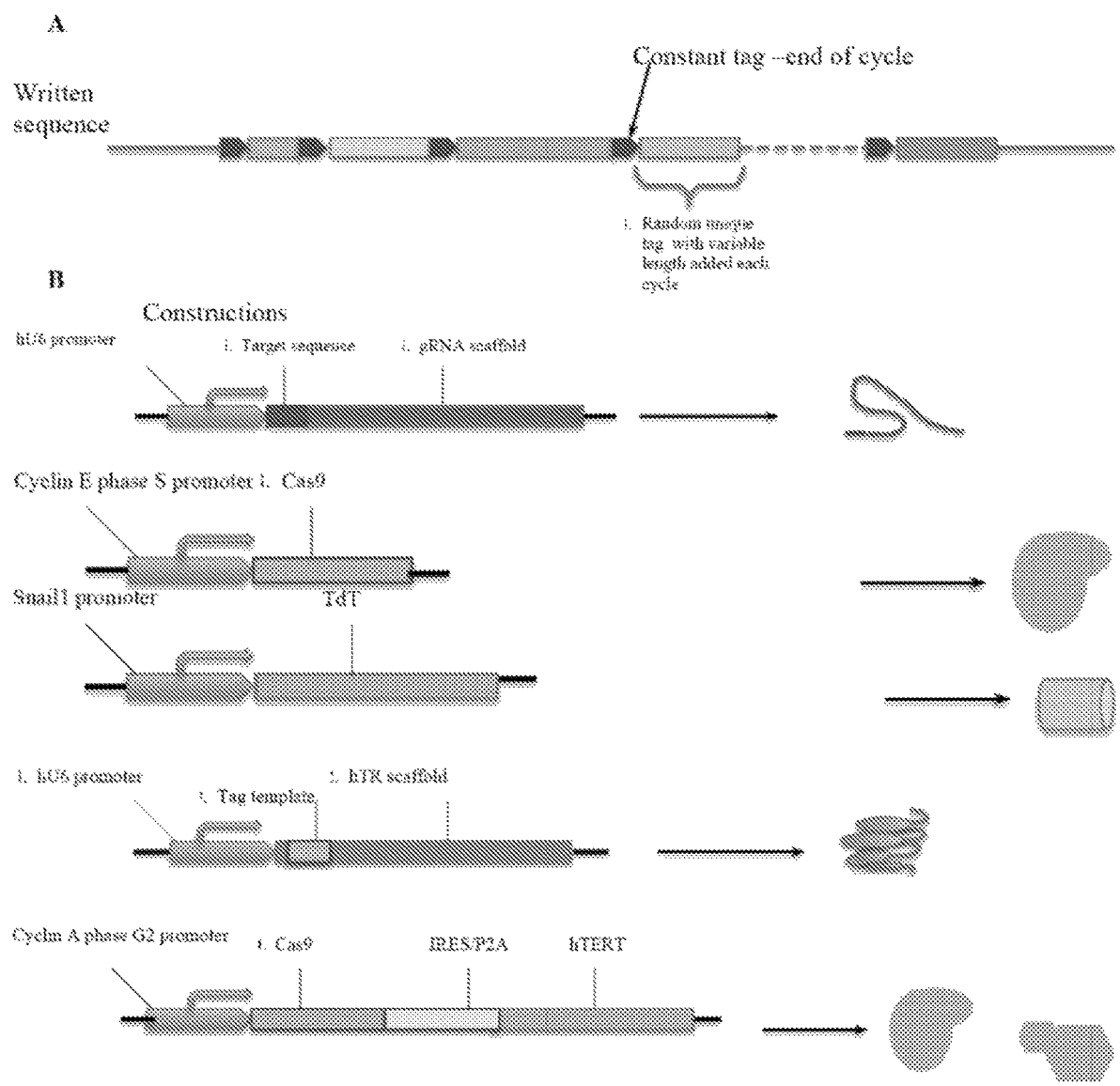
FIG. 13. Depicts the construction and working scheme of written sequences in MCDS 3. This system is a basic molecular cell diary system and can be used for lineage tracing, family tree construction, biological clock/timing and dynamic cellular activity history. At the start of a cellular event, a combination of a DNA cutter and a DNA writer under the control of the event-specific promoter (e.g. cyclin E for $G_1$-S phase of the cell cycle) a random, unique barcode with variable length is written, followed by a constant nucleotide tag written by a second DNA cutter and writer combination to mark the end of the event. The length of the random barcode is linearly correlated with the activity of the gene promoter of interest. The construction is similar to MCDS 2B, except that the promoter that drives TdT is sensitive to the start of an event of interest (e.g. Snail1 promoter is activated at EMT initiation. SNAIL1 is critically required for epithelial cells migration such as during local invasion of cancer cells).

MCDS 3 (FIG. 13A): MCDS 3 provides a simple MCDS for lineage tracing and family tree construction, event timing, and cellular activity history. The recording unit structure for this system is similar to MCDS 2, a random unique barcode and a constant tag. In MCDS 3 random unique barcode lengths vary depending on the signal strength of the cellular activity of interest, for example, the promoter activity of a particular gene. The maximum length of the random barcode is between about 50-200 bp so that the total length of a written sequence does not greatly exceed 10 kbp, which in turn allows efficient and reliable PCR amplification of the written sequence and subsequent next generation sequencing.

Figure 14:
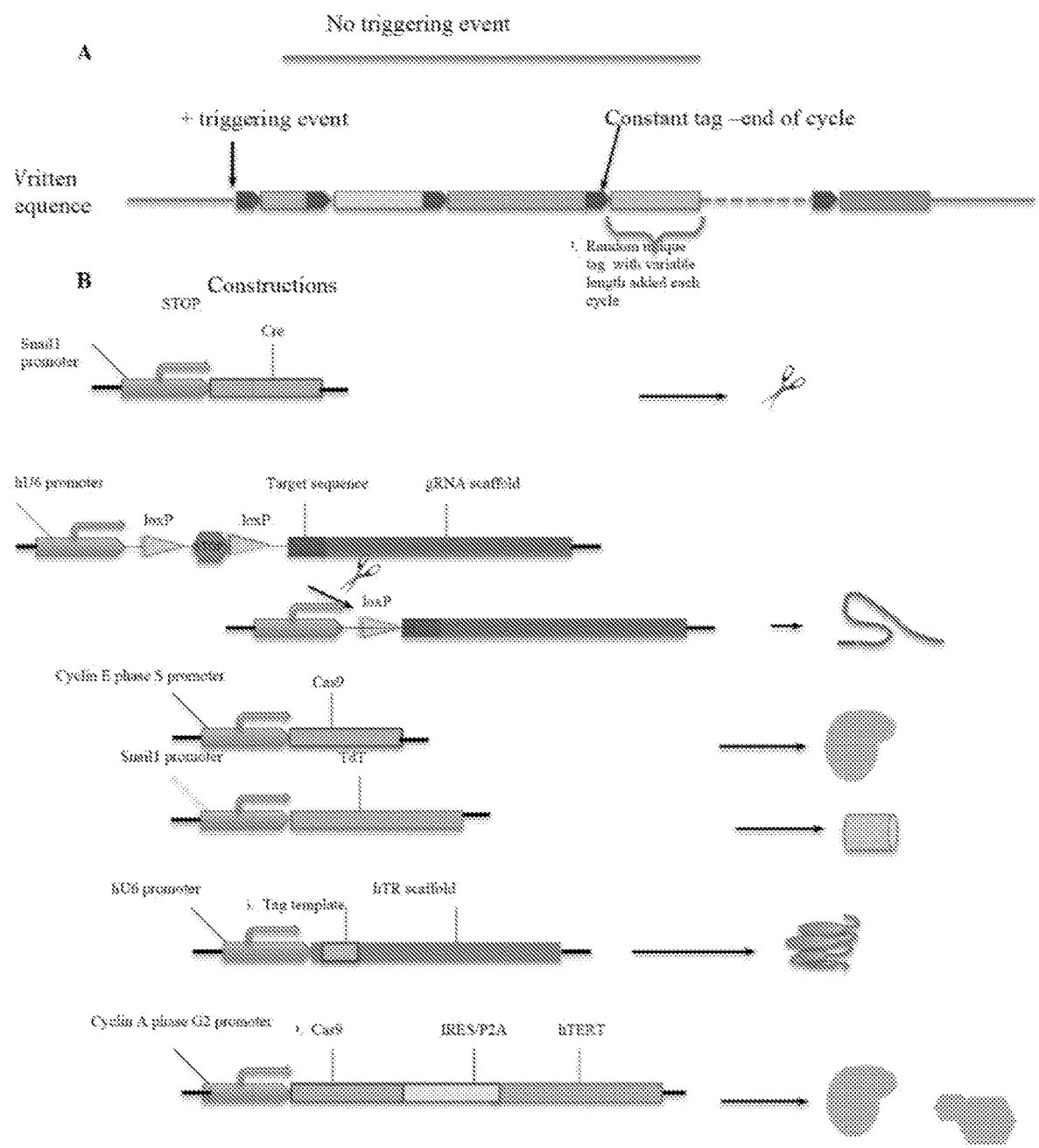
FIG. 14. Depicts the construction and working scheme of written sequences in MCDS 4. This system is a trigger-based molecular cell diary system that is activated when certain biological events occur. The written sequence is the same as in MCDS 3, except that the writing begins only when a molecular trigger of interest starts. To accomplish this, 2 additions to MCDS 3 are made as follow: 1) A Cre recombinase cassette is driven by a promoter specific for the signal of interest, e.g. SNAIL1 promoter for EMT initiation and local invasion, and 2) A loxP-polyA/STOP-loxP cassette is inserted into the hU6 promoter driving expression of the finder (gRNA). When the Snail 1-dependent invasive signal is initiated, Cre is expressed, which in turn removes the STOP signal allowing gRNA to be constitutively produced. Upon the cell reentering and exiting the cell cycle after SNAIL1 activity subsides, the 2 cyclin promoter-driven cutter-writer constructs will add a random, unique barcode and an end-of-cycle constant tag, similar to MCDS 3.

MCDS 4 (FIG. 14A): MCDS 4 provides a cellular event triggered MCDS. The structure of this system is similar to MCDS 3, except that the recording is triggered by certain cellular events of interest, such as developmental milestones or metastatic initiation.

Figure 15:
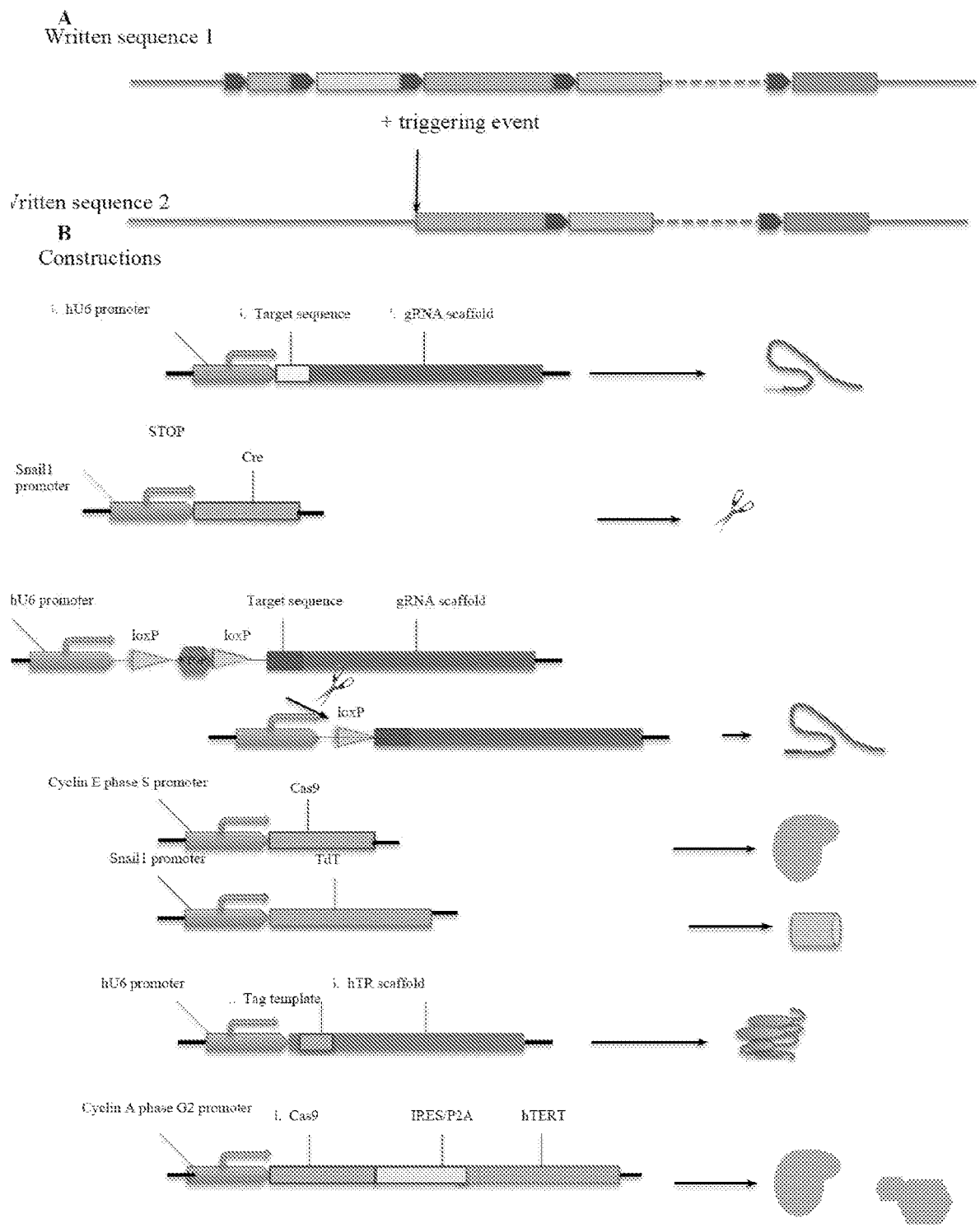
FIG. 15. Depicts the construction and working scheme of written sequences in MCDS 5. This system is a comprehensive MCDS combining MCDSs 3 and 4 so that all components (e.g. lineage tracing, biological clock/timing, dynamic activity history) can be activated simultaneously and record their respective sequences into different target sequence sites.

MCDS 5 (FIG. 15A): MCDS 5 provides an all-in-one MCDS, combining MCDS 3 and MCDS 4. MCDS 5 allows for simultaneous monitoring of most cellular activity of interest (MCDS 3) and recording predefined cell events as they begin.

EXAMPLE 2

Practical Aspects of MCDS

For massively parallel DNA sequencing, written sequences are first amplified by single cell targeted PCR and then read by NGS in a multiplex sequencing platform, such as. barcode sequencing with single or double indexing. Additional examples of NGS and multiplex sequencing setups are well known to a person of ordinary skill in the art and such embodiments are within the purview of the invention.

The number of cells analyzed can range from $10^4$ to $10^6$ with current high-throughput technologies. In the case of cell cycle-based biological clock, assuming the number of cell divisions is less than 50 (i.e. average of 15 for normal cells and 50 for transformed cells), the constant end tag is 8 bp and the average unique barcode size is 100 bp, the average size of written sequences will be $(100+8)*50 =5400$ bp. With the average number of cells to be analyzed of $10^5$ at 10× sequencing depth, the total bp read will be 5400× $10^5 \times 10 = 5.4 \times 10^9$ bp, which can be accomplished within days with current sequencing platforms.

EXAMPLE 3

MCDS in Tumor Dormancy

Tumor dormancy is a significant and poorly understood clinical problem. It is defined as the presence of clinically silent and resistant cancer stem-like DTCs. Therapeutic strategies to eliminate dormant DTCs have been elusive because of their rarity and a dearth of actionable targets. A SNAIL1-induced EMT mouse model was developed. SNAIL1 plays a role in breast cancer metastasis. In the SNAIL1-induced EMT mouse mice, the presence of dormant DTCs was demonstrated.

Dormant DTCs share several parallels with cancer stem-like cells, with overactive survival and stress-induced p38MAPK pathways and EMT activation. DTCs can arise from premalignant lesions (early DTCs) and established tumors (late DTCs). Early and late DTCs appear to differ in their potential for dormancy maintenance and eventual reactivation of growth with early DTCs tending to have longer dormancy periods, presumably due to their arising from lesions with lower burden of somatic changes compared to late DTCs. Therapeutic success depends on the ability to target both DTC populations, which requires identifying all driver somatic alterations at each DTC milestone, namely, emergence from primary tumor, migration, dormancy in secondary organs, and MET to form metastases. MCDS can be applied to a DTC to obtain a detailed molecular history of a cell makes.

To study early and late DTCs, breast tissue with early dysplastic changes and breast tumors were isolated and briefly dissociated. Cells were then transfected with lentiviral vectors carrying a MCDS as detailed in FIGS. 1 to 4 and eGFP for easy isolation, before being implanted in the mammary fat pad of a normal syngeneic host to form breast tumors. The cells carrying MCDS can be recovered from the mouse and the molecular history of these cells can be determined based on sequencing techniques described above.

In another embodiment, a genetic animal model carrying a MCDS is also envisioned. The animal model can be an animal routinely used in cancer research, for example, mouse, rat, cat, dog, pig, bovine, or a non-human primate. The CRISPR/Cas9 system can be used to introduce multiple constructs in an animal at the same time.

In another embodiment, the MCDS animal model is a conditional model to allow MCDS to be activated when desired, for example, in a tissue-dependent, time-dependent, or a inducer-dependent manner.

The MCDS animal model can be crossed with a breast cancer model. Once lung metastasis is observed, for example, by time lapse or physiologic signs such as hyperventilation, rough coat, weight loss, etc., various tissues, for example, primary tumors, DTCs and lung metastatic tumors, can be collected by eGFP sorting, and single cell genomic and RNA sequencing can be performed.

PCR amplification of MCDS-written sequences and total mRNA at the single cell level can be studied by NGS. A detailed family tree of breast tumor cells from the primary tumor to the intermediary dormant DTCs to metastatic tumors can be constructed based on the combination and order of recorded units of the random, unique barcode and constant tag of the lineage tracer (FIG. 5). Building around the tree, the timing and signal amplitude (biological clock and trigger event recorder) of critical events along the tumor progression timeline such as EMT initiation (e.g. SNAIL1), EMT maintenance followed by reactivated growth of dormant DTCs (e.g. interruption followed by resumption in the cell cycle counter), and accelerated growth of metastatic foci can then be inserted. Finally, the complete genetic and epigenetic maps from the single cell genomic analysis are fed into the tree. With robust statistical platforms, a complete picture of genetic and epigenetic evolution of breast cancer progression will be obtained (FIG. 5). Driver changes at critical transitions will become more evident, which will then accelerate subsequent biological validation and therapeutic development.

EXAMPLE 4

Other Examples of the Applications of MCDS

MCDS can be used for detailed lineage tracing of cellular identity and creation of a cellular family tree in vivo. For example, a genetic model is engineered to carry MCDS 2. To determine all cell identity of a tissue of interest (e.g. the heart), cardiac cells are harvested and separated into single cells either by FACS or limiting dilution. The written barcode sequences of individual cells are amplified by single cell PCR. The PCR products are further labeled with barcode adapters to mark the cellular source of each PCR product, then pooled together for next generation DNA sequencing.

Based on the written sequences, not only lineage relationship but also generational relationship between individual cells can be precisely defined.

When combined with single cell DNA and RNA sequencing to determine mutational burden and gene expression levels, MCDS can be applied to map the evolution of cellular signals from start to end of key cellular processes such as cell fate decisions and temporal determinants of functional outcomes. Specifically, once the cellular family tree of cells in a tissue is created and single cell DNA/RNA sequence profiles are available for these cells. A 3-dimentional congregation map can then be drawn in which the x-axis represents the number of cell cycle number, the y-axis the expression level or genetic alteration of a gene, and the z-axis the generational cellular relationship based on lineage barcode identity. Using this approach, the dynamics of genetic and epigenetic changes during development can be identified with high confidence for faster biological validations.

In normal tissue development, it is critical to be able to draw a cell development tree for all cells in that tissue or animal, similar to the lineage cellular tree of *C. elegans*. This information will help identifying rare, transient subsets of cells that may play important roles in lineage commitment factors at transition stages of tissue development, e.g. the fate transitions from cardiac tissue stem cells to cardiomyoblasts and then to cardiomyocytes. In immunology, these systems can provide mechanistic insights into immune cell development, differentiation and trans-differentiation.

In tumor biology, the invention can facilitate the determination of the origin of tumor cells and stromal cells in tumor, i.e. cancer stem cells vs. recruited systemic cells, and help to identify master regulators at each time point of tumor progression: cellular transformation, tumor growth, cancer EMT activation, local invasion, tumor dormancy and reactivation of dormant tumor cells to form macrometastases (See Example 3).

EXAMPLE 5

MCDS in Clinical Diagnosis

In human cancer patients, detection of microscopic DTCs is critical for correct prognostic stratification, appropriate treatment strategy and long-term surveillance. However due to their rarity, detection can be very difficult. Even if these DTCs could be reliably isolated, it is extremely challenging to identify and understand driver genetic and somatic changes that may represent therapeutic targets. The MCDS can be applied to achieve this goal. Replication-incompetent viruses expressing the MCDS can be injected directly into the primary tumor during biopsy to introduce the MCDS into some tumor cells a few days prior to the planned open surgical resection. At the time of and after surgery, blood and bone marrow samples are obtained and total nucleic acids are isolated from nucleated cells. Written barcode sequences are amplified from genomic DNA and total RNA isolated from the primary tumor, peripheral cells, and subjected to NGS. This method can reveal not only the presence of these rare DTCs but also the number of cell divisions, expression profiling and mutational history of these DTCs as compared to the primary tumor. From there, potential genetic and somatic driver alterations may become evident.

EXAMPLE 6

MCDS Containing a DNA Writer that Writes Constant DNA Tag Sequences

Understanding cell-fate and cell to cell interactions in vivo requires a system that allows for comprehensive records of a cell's life, particularly, important genetic and epigenetic changes that occur as each cell evolves through successive generations. Current technologies only allow for single capability and thus provide a more limited view of a cell's fate and history. For example, some of the current approaches use fluorescently labeled proteins, fixed DNA barcoding and the genomic editing tool CRISPER/Cas9. An example of fluorescent protein-based lineage tracing is the BRAINBOW technique in which hundreds of different hues were generated to label distinct neuronal lineages to study brain organogenesis by randomly combining a small set of different fluorescent proteins. Although very useful, the main drawback is its modest resolution due to limited numbers (usually hundred) of non-overlapping colors that can be generated. In contrast, fixed DNA barcoding has far higher coding capacity—up to 500,000 different cell lineages.

In addition, the use of the unique enzyme hTERT to generate the constant end tag only adds a short fragment (6-8 nucleotides in length). With the additions of short fragments, the overall size of the entire insert is kept within a manageable range. As such, the introduction of the constant tag greatly enhances the tracking capacity of MCDS in complex organisms compared to existing technologies. When combined with the random barcoding component and single cell genomics, it allows MCDS to pinpoint gene networks controlling each cell fate transition with high accuracy and confidence.

EXAMPLE 7

Advantages of MCDS over Current Technologies

Figure 16:
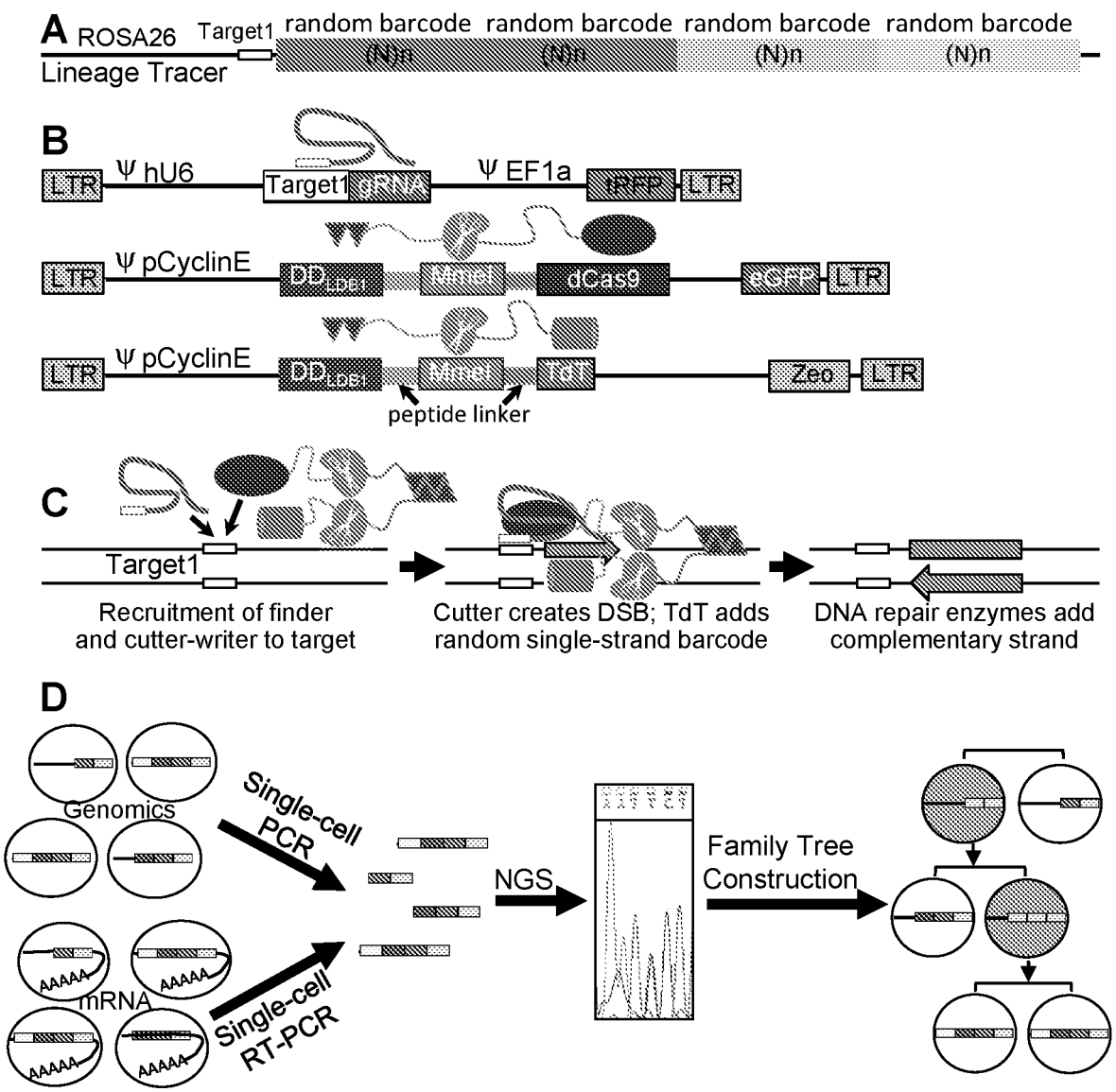
FIG. 16. A basic MCDS lineage tracer. (A) Diagram of concatenated variable barcodes written at a target site. (B) Components of a basic lineage tracer. The hU6 promoter-controlled finder (gRNA) recruits the cutter (dCas9-Mme1-$DD_{LDB1}$), which then brings the writer (TdT-Mme1-$DD_{LDB1}$) to the DSB through the dimerization domain $DD_{LDB1}$. Both cutter and writer are under cyclin E promoter, which is active at the $G_1$-S transition. (C) Schematic of a lineage tracer. The finder binds the target and recruits the cutter-writer complex. The cutter creates a DSB, allowing the writer to add a random sequence. DNA repair machineries add the complementary strand. The process is repeated at each $G_1$-S transition. (D) Sample workflow of the lineage tracer. Barcodes (4 in this example) amplified by PCR (genome) or RT-PCR (mRNA) are subjected to NGS. A cellular family tree is constructed based on barcode sequences. Grayed out cells are parental cells that no longer exist. In large scale experiments, barcode identity can be extracted from WES and RNAseq with or without first amplifying the barcodes separately.
Figure 19:
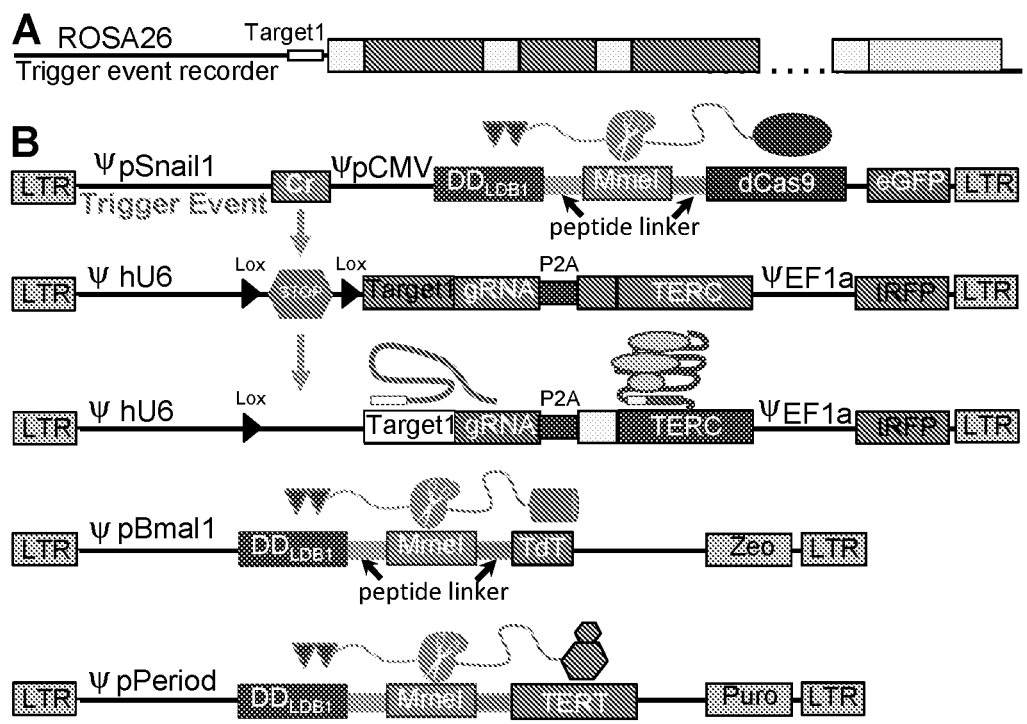
FIG. 19. A Single-Use On-Switch Trigger Event Recorder. (A) Diagram of recording units of a single On-switch trigger event coupled with a reference biological clock. (B) Constructs of a Trigger Event Recorder, e.g. EMT initiation by Snail 1. Upon EMT, Cre is expressed and cleaves the lox-Stop-lox cassette to turn on the finders. The pCMV promoter drives constitutive expression of the cutter dCas9-Mme1-$DD_{LDB1}$. The writer complexes are driven by oscillating promoters of the circadian rhythm (Bmal1 & Period). The triggered finders then set off recording by oscillating cutter-writer complexes.
Figure 20:
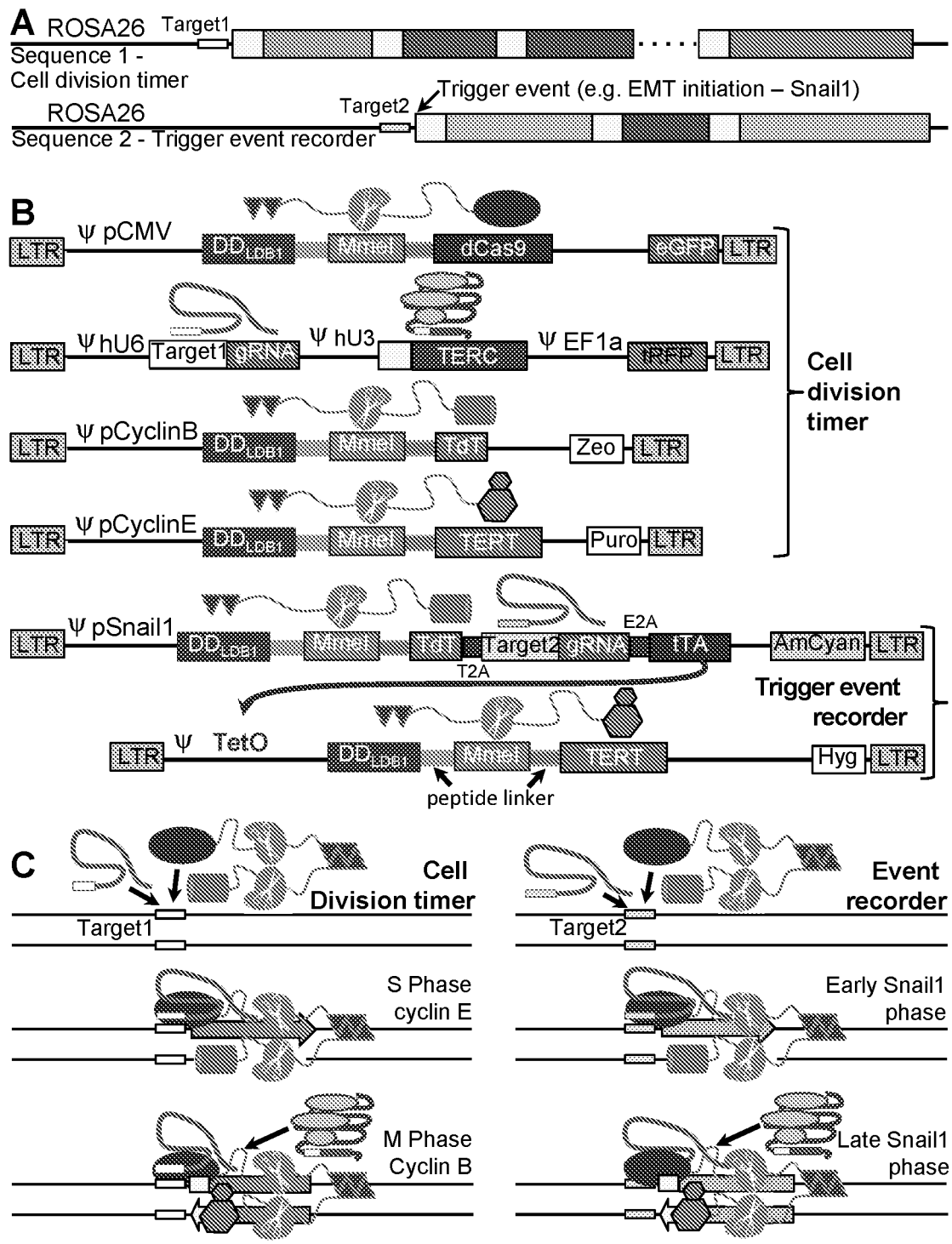
FIG. 20. Multi-functional MCDS. (A) Diagram of recorded units of a variable barcode and a constant tag written on 2 different sites for 2 different purposes. Repeated events are recorded as concatenated units. (B) Cell division timer (CDT) and Trigger event recorder (TER). The pCMV promoter drives constitutive expression of dCas9-Mme1-$DD_{LDB1}$. CDT uses sequential cyclins E and A promoters to drive the cutter-writer complexes (TdT-Mme1-$DD_{LDB1}$ and TERT-Mme1-$DD_{LDB1}$ for variable and constant barcode, respectively). TER uses a sequential, multi-use On/Off switch, in which Snail 1 promoter drives TdT-Mme1-$DD_{LDB1}$ (variable barcode) and gRNA for a second target. Tet-off transactivator (tTA) is co-expressed with TdT-Mme1-$DD_{LDB1}$, and if no dox, activates TetO to drive TERT-Mme1-$DD_{LDB1}$ (constant tag). (C) Schematic of multi-function MCDS on several target sites.
Figure 21:
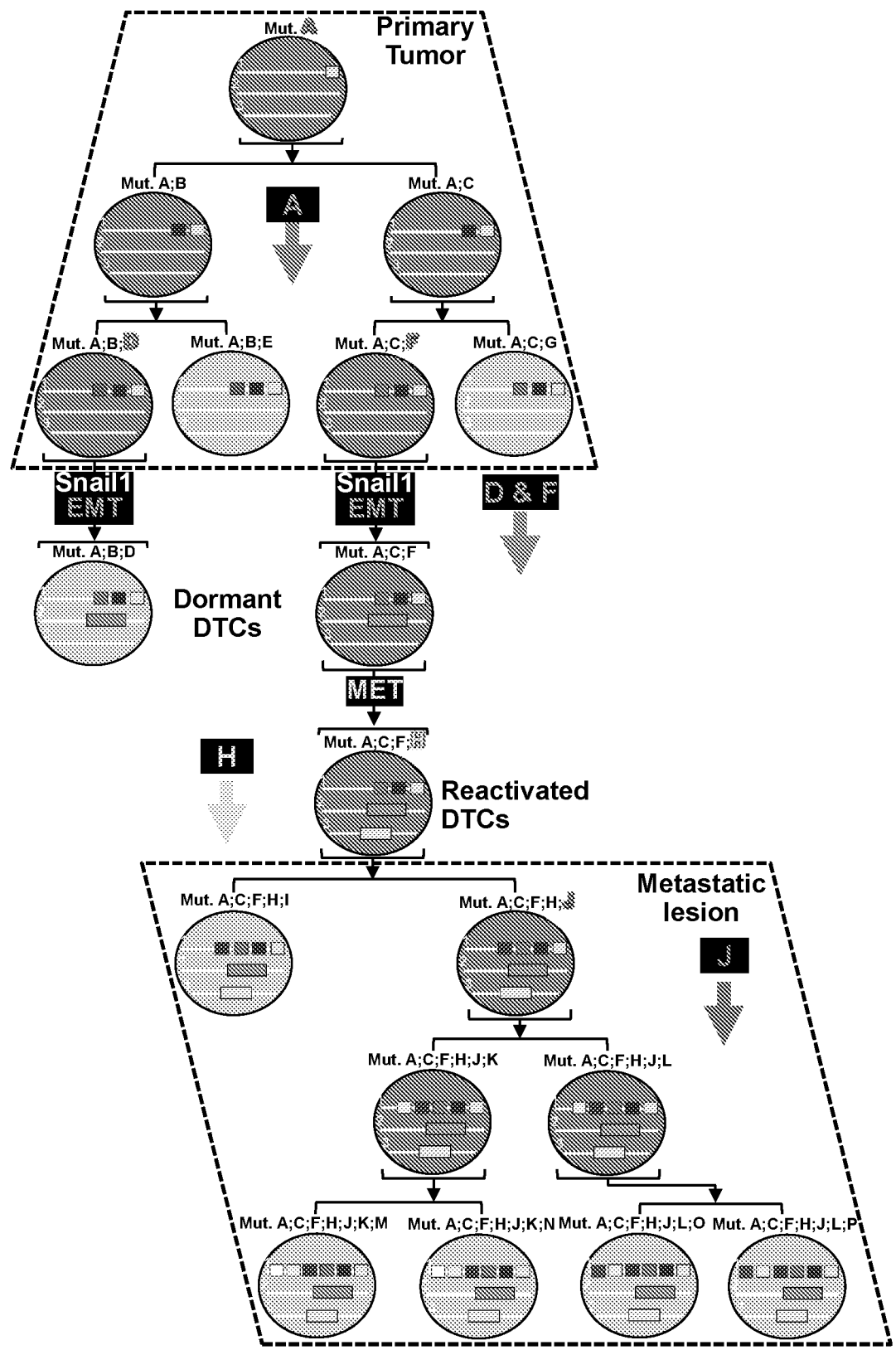
FIG. 21. A potential application of MCDS when combined with single cells' NGS and RNAseq to identify driving genetic and network mutations at milestones of breast cancer progression. Here, a detailed cellular family tree is constructed based on NGS of random barcodes recorded on 3 sequences. Sequence 1 is for cell cycle counting, 2 for EMT/Snail 1 triggered recording, 3 for MET-triggered recording. Integration of genetic and networks alternations identifies potential driving changes. In this example, eGFP-labeled tumor cells are used for sorting. Pale green cells no longer exist. Mutation A is likely a driving change (downward arrows) for primary tumor growth; Mutations D an F for Snail 1-initiated EMT; Mutation H for MET; and Mutation J for growth of metastatic tumors, respectively.

A system is provided for cell-based studies that can effectively mitigate many of the deficiencies of current techniques. The system employs massively parallel monitoring of individual cells in vivo and includes information on cell lineage, biological timing, and molecular activity memory, all at the single cell level. The lineage tracing data can construct detailed cell family trees (FIGS. 16 and 21). The biological timer is based on oscillators such as the cell cycle and the circadian rhythm (FIG. 19). Molecular activity memory recorder is triggered by an event, e.g. fate decision or EMT initiation (FIGS. 16-17, 19-20). This system significantly improves the understanding of normal development, tissue maintenance, and diseases like cancer at the single cell level.

The genome-editing tool CRISPR/Cas9 or TALEN technology is used to provide site specificity for DNA barcoding. Cas9 or TALEN (the DNA cutter) expression is controlled by event-specific promoters (e.g. cyclins for the cell cycle or Snail1 for EMT initiation). At each cutter-created DSB, a constant tag or a combination of a random barcode and a constant tag is inserted by one or more DNA writers that are co-expressed with the DNA cutter. The writer is either a template-independent DNA polymerase, e.g. TdT, which synthesizes a random single-stranded DNA fragment, or a template-dependent polymerase, e.g. telomerase, which adds a constant tag, for example, GGTTAG. Endogenous DNA synthetic and repair mechanisms (e.g. NHEJ or HDR) synthesize complementary strands and seal the DSB. To build a cellular clock and event recorder, insertion of the constant tag, optionally, in combination with a random tag, is sequential to mark the beginning and end of the event, respectively. This is achieved by selecting event-specific promoters that are sequential (e.g. cyclins E and A for the $G_1/S$ and $S/G_2$ phases of the cell cycle, respectively), or that can be engineered to be sequential (FIG. 20). These tags are unique and can be aligned with the internal reference oscillators to determine the event timing.

Components of MCDS: A target guide coupled with a nuclease (the finder-cutter), and a DNA polymerase (the writer). Finder-cutters' role is to create a DSB at specific locations to allow the writer to add nucleotides. They are genome editing nucleases such as the CRISPR/Cas9, the TALEN and the Zinc Finger Nucleases (ZFN).

The Finder-Cutter Head: With its high site specificity and ease of use, CRISPR/Cas9/gRNA is a preferred finder-cutter system for MCDS. However the PAM immediately following the target sequence is necessary for stable Cas9 nuclease binding and destroyed after being cleaved. Therefore the native Cas9 is not suitable for MCDS since it does not allow successive tracking. A customized cutter is created in which a modified Cas9 with its PAM-dependent nuclease domain catalytically inactivated (dead Cas9 or dCas9) is fused with the nuclease domain of the well-characterized PAM-independent nuclease Mme1 (Mme1 generates a 3' protruding DSB needed for the writer, FIG. 16B). A similar construct fusing dCas9 with the nuclease domain of the nuclease Fok1 (dCas9-Fok1) was created and shown to have PAM-independent specific genome editing activity.

Fok1 nuclease requires homo-dimerization. To achieve site-specific dimerization, two molecules of dCas9-Fok1 were brought into close proximity using two gRNAs specific for two closely spaced target sequences. In such set-up, two closely spaced target sequences are identified to indicate each time a random barcode is inserted. Alternatively, well-characterized protein dimerization domain of the Lim Domain Binding protein ($DD_{LDB1}$) fused with Mme1 ($dCas9-Mme1-DD_{LDB1}$) was used. A second construct that expresses $Mme1-DD_{LDB1}$ can provide the dimerization substrate through $DD_{LDB1}$ for optimal Mme1 nuclease activation (FIG. 16B).

TALEN or ZFN: The advantage of these systems is that these systems do not require gRNA and PAM motif. A new complex may be designed for each target sequence. TALENs are generated by fusing a TAL effector DNA-binding domain to a DNA cleavage domain such as Mme1 or Fok1. ZFN also use the same nucleases fused to engineered Cys2His2 zinc fingers that function as specific DNA binding domain, recognizing different nucleotide triplets. ZFN may have higher off-target effect compared to the former two systems.

The Writer Heads: Writer heads are DNA polymerases that can add nucleotides to the target DSB in either a template-dependent or -independent manner. The processivity of the writer head should ideally be low (i.e. adding 20-200 bp per recording) because high processivity leads to excessive barcode length, lower PCR efficiency and high sequencing cost. Barcode length may be kept relatively constant by fusing the cutter to the writer by a flexible linker. The cutter anchors the fusion complex at the target site as the writer adds nucleotides until the length of the barcode approximates that of the linker, at which time the writer stops (FIG. 16). However DNA flexibility may allow the writer to continue (See below for further discussion).

Template-independent Writers in MCDS. They add random sequences to store information on unlimited numbers of cellular events. One example is TdT, a specialized, low processive DNA polymerase responsible for increasing junctional diversity in lymphocyte antigen receptors by introducing short stretches of random nucleotides, and also widely used in molecular biology for inserting nucleotides to ends of DNA sequences (FIG. 16B). TdT prefers a 3' protruding DSB to a blunt-end or 3' recessed DSB, although at high concentrations it can incorporate nucleotides efficiently to all three types of DSB. To maximize efficiency, Mme1 is preferred as it generates a 3' protruding DSB, whereas Fok1 creates a 3' recessed DSB. The low processivity of TdT is ideal for MCDS to limit the size of the barcodes manageable for subsequent PCR-amplification and analysis.

TdT (writer) can be fused with the $Mme1-DD_{LDB1}$ (cutter) to generate $TdT-Mme1-DD_{LDB1}$, which when co-expressed with $dCas9-Mme1-DD_{LDB1}$ and ROSA26-specific gRNA, ensures ready access of TdT to the Mme1 dimer-generated DSB for efficient barcode insertion while minimizing steric competition from endogenous DNA repair complexes (e.g. NHEJ) when recruited to the DSB. Endogenous DNA repair machineries then mend non-complementary, overlapping, TdT-synthesized, single-stranded sequences, and seal the DSB to create the full-length barcode (FIG. 16C). Each barcode is unique, thus providing an infinite tracking capacity.

Template-independent DNA polymerases include the X-family DNA polymerases, although they have higher processivity and other DNA repair functions that may be difficult to control compared to TdT. Cell lineage construction is based on sequence identity alignment and a representative cell family shown (FIG. 16D). Because the target sequence is located within the ROSA26 locus, a constitutively open locus, barcode clusters can also be amplified from a cDNA library of total mRNA (FIG. 16D). This capability allows integration of genomics, expression profiles and lineages in one RNA sample.

Figure 17:
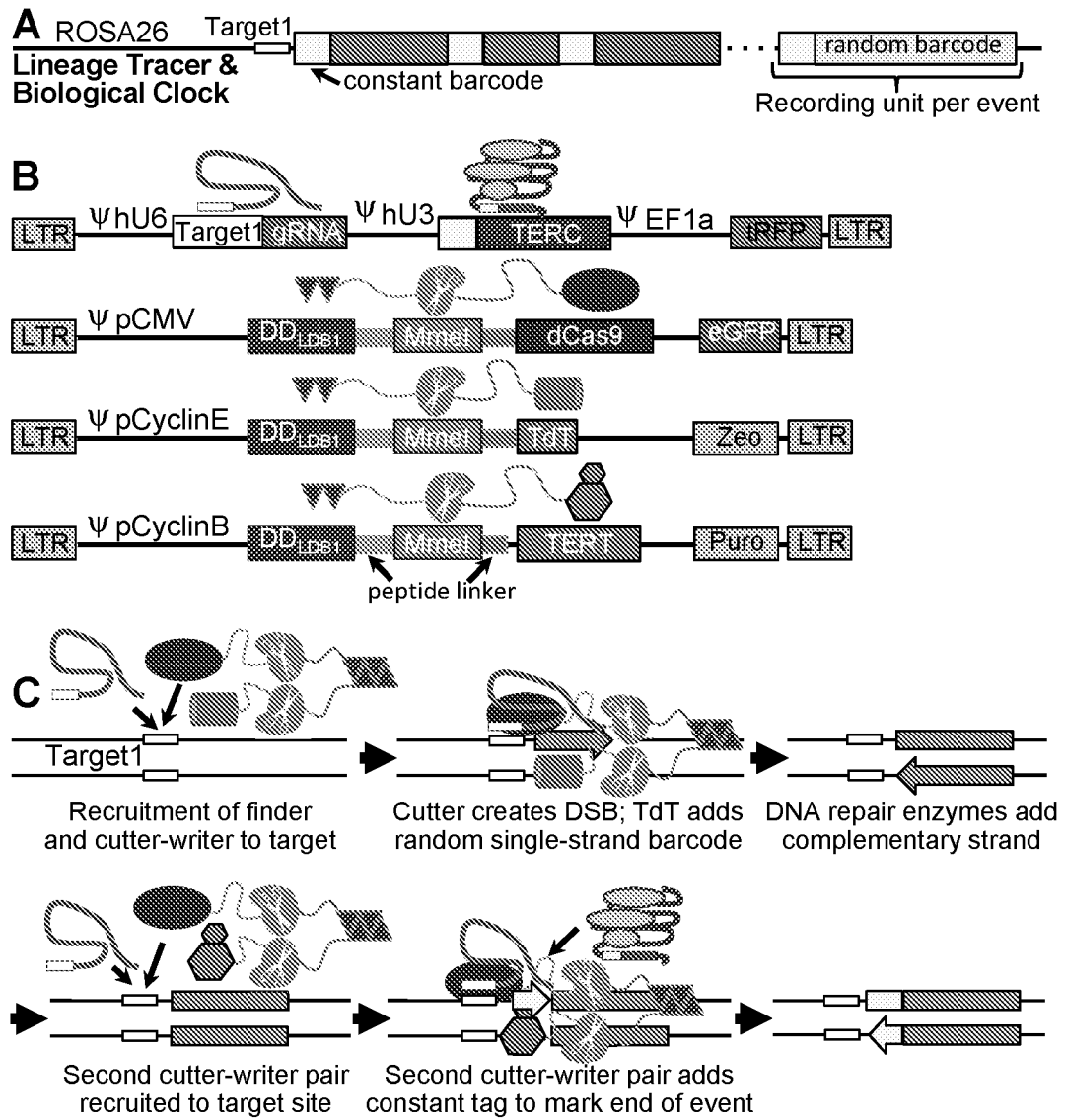
FIG. 17. A Combined Lineage Tracer and Biological Clock. (A) Diagram of recording units consisting of a random, unique barcode (lineage tracing) and a constant tag (marking the end of an event-clock) written at a target site. (B) Constructs of a combined MCDS Lineage Tracer and Biological Clock. The pCMV promoter drives constitutive expression of dCas9-Mme1-$DD_{LDB1}$. The biological clock uses sequential cyclin E and B promoters driving the TdT-Mme1-$DD_{LDB1}$ (random barcode) and the TERT-Mme1-$DD_{LDB1}$ (constant tag) to mark the beginning and end of the event, respectively. (C) Schematic of the double-function MCDS on the target site.
Figure 18:
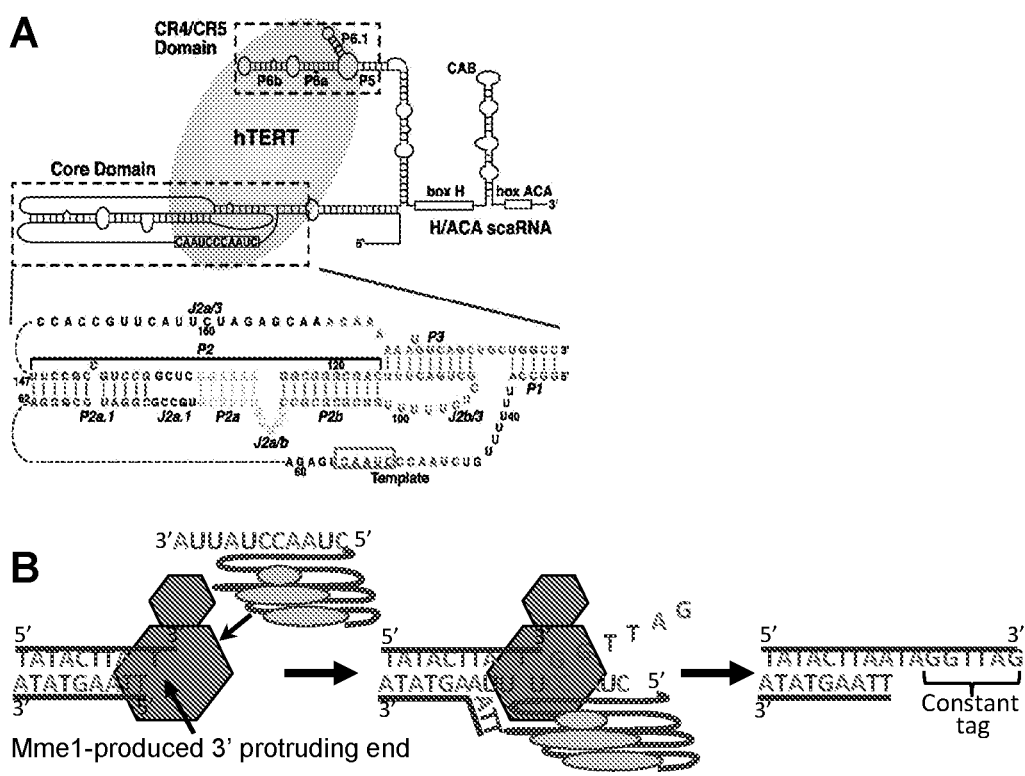
FIG. 18. TERT Optimization. (A) In vertebrates, TERC carries the template 3'-CAAUCCCAAUC-5' (SEQ ID NO: 1). TERT adds the sequence 5'-TTAGGG-3' to the 3' chromosome end by pairing with the template. (B) Diagram of the modified TERT/TERC system. The dCas9-Mme1 cutter cleaves at a fixed site (FIG. 17B) to generate a 3' protruding end. We replace the 3'-CAAUC-5' end of TERC (rectangle in A) with 3'-AUUAU-5', which pairs with the 3' end of Mme1-created DSB. TERT adds a constant tag using the modified template. DNA polymerase fills the gap.

Writer heads that add constant tags and require a template: The template preferably is RNA so it does not interfere with the DNA sequence to be written. In essence, these are reverse transcriptases (RT). Of particular interest is telomerase (FIG. 17). Telomerase is a ribonucleoprotein polymerase TERT that catalyzes the 3' extension of telomeric DNA in eukaryotes with a tandem repeat of a constant sequence using a single-stranded RNA molecule TERC as a template. In vertebrates, by using the template 3'-CAAUCC-CAAUC-5' (SEQ ID NO: 1) carried by TERC, TERT can add 5'-TTAGGG-3', a six-nucleotide repeating sequence to the 3' strand of chromosome (FIG. 18A). This process is dependent on the binding of the first few 3' nucleotides of the template to the last telomere sequence. In MCDS, although the telomerase complex has already been localized to 3' end of the DSB by its fusion with dCas9, optimization may be required to ensure adequate telomerase activity at a non-telomere 3' end of DNA. Because the dCas9-Mme1 cutter most likely cleaves at a fixed location, the 3'-CAAUC-5' nucleotide 57-61 of TERC (red rectangle in FIG. 18A) were replaced with 3'-AUUAU-5', which pair-matches with the 3' end of Mme1-created DSB. TERT then extends using the template to add a constant tag (FIG. 19B). Alternatives to telomerase are retrotransposable elements and retroviral RT. These fragments tend to be larger, for example, several kilobases, and may be engineered to be used in place of telomerase.

Control/regulatory elements: These are promoters that regulate the timing, duration and amplitude of expression of the DNA cutters and DNA writers in response to certain cellular events. Timing elements of great interest to MCDS are oscillating clocks such as the cell cycle (FIGS. 16-17 and 19-20), the circadian rhythm (FIG. 19), the segmentation clock, and the p53 and Ca ion oscillators. Recently, artificial genetic oscillator circuits were introduced into cells with positive and negative feedback and time delay. The oscillatory frequency and amplitude can therefore be tunable to fit the needs of different MCDS versions. For a better integration of these special properties of MCDS, an On/Off switch must be constructed that can be used once or repeatedly depending on the need.

Single-use On/Off Switches can be constructed using recombinase systems like Cre-loxP and Flp-FRT. For example, expression of gRNA and TERC can be regulated by positioning a pair of loxP sites at strategic locations. For the "On switch", a cassette containing a polyA stop signal flanked by 2 loxP sites (LSL) can be inserted in the hU6 promoter region. When the recombinase Cre is expressed in response to EMT initiation, the LSL cassette is excised, thereby permanently turning on the finder (FIG. 19). For the Off switch, the entire finder gene is flanked by 2 loxP sites allowing the gene to be permanently inactivated by Cre. The cutter and writer are separately driven by a Snail-1-independent time oscillator like the circadian rhythm and as a result EMT initiation will be captured either at the beginning (On) or end (Off) of barcode recording in reference to the circadian rhythm.

Multi-use On/Off Switches are constructed with event-specific promoters that are sequential to ensure that the constant tag is only added after the random barcode has been completed (e.g. cyclins E and A for the $G_1/S$ and $S/G_2$ phases of the cell cycle, respectively), or that are engineered to be so. For example, expression of the first random writer TdT and the tet-off transactivator tTA is linked to EMT initiation/Snail-1. The second writer TERT is not expressed until tTA activates the TetO promoter in the absence of doxycycline (FIG. 20), thus a time delay between the two writers is introduced. TdT's random barcode reflects the duration and amplitude of the Snail-1 promoter activity, while TERT marks the end of the event with a constant tag. For tighter control, an shRNA specific for the first writer can be added to the second writer construct, in which the constant tag will truly mark the end of the first event. However some signal dynamics may be lost since the first writer's promoter may still be active when the shRNA is expressed.

MCDS in tumor dormancy and beyond: Tumor dormancy is a significant and poorly understood clinical problem. It is defined as the presence of clinically silent and resistant cancer stem-like DTCs. Therapeutic strategies to eliminate dormant DTCs have been elusive because of their rarity and a dearth of actionable targets. A Snail 1-induced EMT mouse model was used to demonstrate a critical requirement for Snail-1 in breast cancer metastasis. In these mice, the presence of dormant DTCs was also demonstrated. Dormant DTCs share several parallels with cancer stem-like cells, with overactive survival and stress-induced p38MAPK pathways and EMT activation. DTCs can arise from premalignant lesions (early DTCs) and established tumors (late DTCs). Early and late DTCs appear to differ in their potential for dormancy maintenance and eventual reactivation of growth with early DTCs tending to have longer dormancy periods, presumably due to their arising from lesions with lower burden of somatic changes compared to late DTCs. Therapeutic success would depend on the ability to target both DTC populations, which requires identifying all driver somatic alterations at each DTC milestone (i.e. emergence from primary tumor, migration, dormant DTCs, and reactivation of DTCs to form metastases or the mesenchymal-epithelial transition, MET). The need to have a detailed family lineage and detailed molecular time capsule at each stage of cancer progression makes tumor dormancy a perfect candidate to which the MCDS described herein can be applied.

To determine the differences between different stages of metastasis and between early and late DTCs, breast tissues with early dysplasia, high-grade dysphasia or invasive tumors, presumably producing early and late DTCs, respectively, can be isolated from the breast cancer model MMTV-PyMT and briefly dissociated. Isolated tumor cells can then be transduced with lentiviruses carrying MCDS as detailed in FIGS. 16-20, and epithelial stem cells can be selected for by puromycin resistance in 3D mammosphere culture to enrich for stem-like cells. The dCas9-Mme1-DD$_{LDB1}$ vector also contains an eGFP cassette, which can be used for visual tracking and isolation. Once lung metastasis is present (by time lapse or physiologic signs such as hyperventilation, rough coat, weight loss, etc.), various tissues (e.g. primary tumors, DTCs and lung metastatic tumors) can be collected by eGFP sorting, and single cell genomic and RNA sequencing will be performed. In WES, barcode information can easily be extracted from the known insertion site. For RNAseq, barcode information can be obtained when they are added to an open, expressed locus, e.g. ROSA26, and deep, paired-end NGS is used. A detailed family tree of breast tumor cells from the primary tumor to the intermediary dormant DTCs to metastatic tumors can be constructed based on the combination and order of recorded units of the random, unique barcode and constant tags of the lineage tracer. Building around the tree, the timing and signal amplitude (biological clock and trigger event recorder) of critical events along the tumor progression timeline such as EMT initiation (e.g. Snail-1), EMT maintenance followed by reactivated growth of dormant DTCs (e.g. interruption followed by resumption in the cell cycle counter), and accelerated growth of metastatic foci can then be inserted. Finally, the complete genetic and network maps from single cell genomic analyses can be fed into the tree. With robust statistical platforms, a complete picture of genetic and epigenetic evolution of breast cancer progression can emerge (FIG. 21). Driving changes at critical transitions will become more evident, which will then accelerate subsequent biological validation and therapeutic development.

In humans, one potential application of MCDS is to mark tumor cells prior to surgical resection by direct intratumoral injection of MCDS carrying viruses. Subsequently written barcode sequences can be amplified from genomic DNA and total RNA isolated from DTCs and primary tumor, and subjected to NGS. This method can detect not only rare DTCs but also their mutational burden compared to the primary tumor. Potential genetic and epigenetic drivers may then become evident and prove useful for personalized precision therapy. Similar applications can also be employed with other complex biological questions such as organ fate determination in animal models where the entire cellular map of an organ can be determined to identify important cell fate decisions that are organ specific, and that are amenable for therapeutic and tissue engineering applications.

MCDS provides several advantages over existing methods, including: 1) a complete all-in-one system that allows for simultaneous recording of information pertaining to cell lineages, biological timing, and cellular and molecular activity dynamics at the single cell level; 2) an ability to track large numbers of cells individually in vivo using random, unique barcodes of infinite variations coupled with massively parallel processing; and 3) a powerful tool to identify critical genetic and or network drivers of events of interest, as revealed when the reconstructed family tree, cell fate history and molecular activity history are aligned with data obtained from single cell analytics. This last point is a particularly powerful potential for MCDS that is much more difficult with other existing methods. The ability to determine generational relationship among cells within a lineage and then to assimilate it with their individual genetic or network profiles means that driving gene networks controlling fate transitions during cell life can be pinpointed with high accuracy and confidence. This in turn allows focused validation experiments to proceed rapidly. MCDS is feasible because it uses well-studied molecular engines that are innovatively integrated to produce massively parallel historical compilation of cellular functions.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Sosa, M. S., Bragado, P. & Aguirre-Ghiso, J.A. Mechanisms of disseminated cancer cell dormancy: an awakening field. *Nature reviews. Cancer* 14, 611-622 (2014).
2. Tran, D. D., Corsa, C. A. S., Biswas, H., Aft, R. L. & Longmore, G. D. Temporal and Spatial Cooperation of Snail1 and Twist1 during Epithelial-Mesenchymal Transition Predicts for Human Breast Cancer Recurrence. *Molecular Cancer Research* 9, 1644-1657 (2011).
3. Tran, H. D., et al. Transient SNAIL1 Expression Is Necessary for Metastatic Competence in Breast Cancer. *Cancer Res* 74, 6330-6340 (2014).
4. Zohn, I. E., et al. p38 and a p38-Interacting Protein Are Critical for Downregulation of E-Cadherin during Mouse Gastrulation. *Cell* 125, 957-969 (2006).
5. Aguirre-Ghiso, J. A., Estrada, Y., Liu, D. & Ossowski, L. ERKMAPK Activity as a Determinant of Tumor Growth and Dormancy; Regulation by p38SAPK. *Cancer Res* 63, 1684-1695 (2003).
6. Alspach, E., et al. p38MAPK plays a crucial role in stromal-mediated tumorigenesis. *Cancer Discov* 4, 716-729 (2014).
7. Carro, M. S., et al. The transcriptional network for mesenchymal transformation of brain tumours. *Nature* 463, 318-325 (2010).
8. Weissman, T. A. & Pan, Y. A. Brainbow: new resources and emerging biological applications for multicolor genetic labeling and analysis. *Genetics* 199, 293-306 (2015).
12. Klein, A. M., et al. Droplet barcoding for single-cell transcriptomics applied to embryonic stem cells. *Cell* 161, 1187-1201 (2015).
13. Macosko, E.Z., et al. Highly Parallel Genome-wide Expression Profiling of Individual Cells Using Nanoliter Droplets. *Cell* 161, 1202-1214 (2015).
14. Rotem, A., et al. High-Throughput Single-Cell Labeling (Hi-SCL) for RNA-Seq Using Drop-Based Microfluidics. *PLoS One* 10, e0116328 (2015).
15. Davenport R J. What controls organ regeneration? Science. 2005 July 1;309(5731):84.
16. Godwin J. The promise of perfect adult tissue repair and regeneration in mammals: Learning from regenerative amphibians and fish. Bioessays. 2014 Sep;36(9):861-71.
17. Hoppe P S, Coutu D L, Schroeder T. Single cell technologies sharpen up mammalian stem cell research. Nat Cell Biol. 2014 October;16(10):919-27.
18. Nimmo R A1, May G E, Enver T. Primed and ready: understanding lineage commitment through single cell analysis. Trends Cell Biol. 2015 May 21. pii: S0962-8924 (15)00083-5.
19. Sandberg R. Entering the era of single-cell transcriptomics in biology and medicine. Nat Methods. 2014 January;11(1):22-4.
20. Wang Y, Navin NE.Advances and Applications of Single-Cell Sequencing Technologies. Mol Cell. 2015 May 21;58(4):598-609.
21. Treutlein B, Brownfield D G, Wu A R, Neff N F, Mantalas G L, Espinoza F H, Desai T J, Krasnow M A, Quake S R. Reconstructing lineage hierarchies of the distal lung epithelium using single-cell RNA-seq. Nature. 2014 May 15;509(7500):371-5.
22. Etzrodt M, Endele M, Schroeder T. Quantitative single-cell approaches to stem cell research. Cell Stem Cell. 2014 November 6;15(5):546-58.
23. C. Blanpain, B. D. Simons. Unravelling stem cell dynamics by lineage tracing Nat. Rev. Mol. Cell Biol., 14 (2013), pp. 489-502.
24. Weissman T A, Pan Y A. Brainbow: new resources and emerging biological applications for multicolor genetic labeling and analysis. Genetics. 2015 February;199(2): 293-306.
25. Levy S F, Blundell J R, Venkataram S, Petrov D A, Fisher D S, Sherlock G. Quantitative evolutionary dynamics using high-resolution lineage tracking. Nature. 2015 March 12;519(7542): 181-6.

26. Bystrykh L V, de Haan G, Verovskaya E. Barcoded vector libraries and retroviral or lentiviral barcoding of hematopoietic stem cells. Methods Mol Biol. 2014;1185: 345-60.
27. Blundell J R, Levy S F. Beyond genome sequencing: lineage tracking with barcodes to study the dynamics of evolution, infection, and cancer. Genomics. 2014 December;104(6 Pt A):417-30.
28. Long Cai et all. Recording and mapping lineage information and molecular events in individual cells. US Patent Application US2015/0225801 A1.
29. Friedland A E, Lu T K, Wang X, Shi D, Church G, Collins J J. Synthetic gene networks that count. Science. 2009 May 29;324(5931):1199-202.
30. Glaser J I1, Zamft B M, Marblestone A H, Moffitt J R, Tyo K, Boyden E S, Church G, Kording K P. Statistical analysis of molecular signal recording. PLoS Comput Biol. 2013;9(7):e1003145.
31. Kording K P. Of toasters and molecular ticker tapes. PLoS Comput Biol. 2011 December;7(12):e1002291.
32. Church G, Shendure J, inventors; Board of the Trustees of Stanford University, assignee (2010) Nucleic Acid Memory Device. United States Patent application: 20100099080.
33. Farzadfard F, Lu T K. Genomically encoded analog memory with precise in vivo DNA writing in living cell populations. Science. 2014 November 14;346(6211): 1256272.
34. Purcell O, Lu T K. Synthetic analog and digital circuits for cellular computation and memory. Curr Opin Biotechnol. 2014 October;29:146-55.
35. Inniss M C, Silver P A. Building synthetic memory. Curr Biol. 2013 September 9;23(17):R812-6.
36. Bonnet J, Subsoontorn P, Endy D. Rewritable digital data storage in live cells via engineered control of recombination directionality. Proc Natl Acad Sci U S A. 2012 June 5;109(23):8884-9.
37. Siuti P, Yazbek J, Lu T K. Synthetic circuits integrating logic and memory in living cells.Nat Biotechnol. 2013 May;31(5):448-52.
38. Farzadfard F, Lu T K. Genomically encoded analog memory with precise in vivo DNA writing in living cell populations. Science. 2014 November 14;346(6211): 1256272.
39. Kim H, Kim J S. A guide to genome engineering with programmable nucleases. Nat Rev Genet. 2014 May;15 (5):321-34.
40. Francisco J., Sanchez-Rivera, Tyler Jacks. Applications of the CRISPR-Cas9 system in cancer biology. Nature Reviews Cancer 15,387-395 (2015).
41. Kleinstiver B P, Prew M S, Tsai S Q, Topkar V V, Nguyen N T, Zheng Z, Gonzales A P, Li Z, Peterson R T, Yeh J J, Aryee M J, Joung J K. Engineered CRISPR-Cas9 nucleases with altered PAM specificities. Nature. 2015 June 22.
42. Bogdanove A J, Voytas DF.TAL Effectors: Customizable Proteins for DNA Targeting. Science 30 September 2011: Vol. 333 no. 6051 pp. 1843-1846.
43. Cermak Ti, Doyle E L, Christian M, Wang L, Zhang Y, Schmidt C, Baller J A, Somia N V, Bogdanove A J, Voytas D F. Efficient design and assembly of custom TALEN and other TAL effector-based constructs for DNA targeting. Nucleic Acids Res. 2011 July;39(12): e82.
44. Fowler J D1, Suo Z. Biochemical, structural, and physiological characterization of terminal deoxynucleotidyl transferase. Chem Rev. 2006 June;106(6):2092-110.
45. Motea E A, Berdis A J. Terminal deoxynucleotidyl transferase: the story of a misguided DNA polymerase. Biochim Biophys Acta. 2010 May;1804(5):1151-66.
46. H. Hwang, J. S. Taylor. Role of base stacking and sequence context in the inhibition of yeast DNA polymerase eta by pyrene nucleotide. Biochemistry 43 (2004) 14612-14623.
47. J. M. Clark, Novel non-templated nucleotide addition reactions catalyzed by procaryotic and eucaryotic DNA polymerases, Nucleic Acids Res. 16 (1988) 9677-9686.
48. J. A. Peliska, S. J. Benkovic. Mechanism of DNA strand transfer reactions catalyzed by HIV-1 reverse transcriptase. Science 258 (1992) 1112-1118.
49. D. Vineyard, X. Zhang, A. Donnelly, I. Lee, A. J. Berdis. Optimization of non-natural nucleotides for selective incorporation opposite damaged DNA, Org. Biomol. Chem. 5 (2007) 3623-3630.
50. B. Devadoss, I. Lee, A. J. Berdis. Enhancing the "A-rule" of translesion DNA synthesis: promutagenic DNA synthesis using modified nucleoside triphosphates. Biochemistry 46 (2007) 13752-13761.
51. M. F. Goodman, S. Creighton, L. B. Bloom, J. Petruska. Biochemical basis of DNA replication fidelity. Crit. Rev. Biochem. Mol. Biol. 28 (1993) 83-126.
52. L. A. Loeb, B. D. Preston. Mutagenesis by apurinic/ apyrimidinic sites. Annu. Rev. Genet. 20 (1986) 201-230.
53. A. Sheriff, E. Motea, I. Lee, A. J. Berdis. Mechanism and dynamics of translesion DNA synthesis catalyzed by the Escherichia coli Klenow fragment. Biochemistry 47 (2008) 8527-8537.
54. S. Shibutani, M. Takeshita, A. P. Grollman, Translesional synthesis on DNA templates containing a single abasic site. A mechanistic study of the "A rule". J. Biol. Chem. 272 (1997) 13916-13922.
55. A. J. Berdis. Dynamics of translesion DNA synthesis catalyzed by the bacteriophage T4 exonuclease-deficient DNA polymerase. Biochemistry 40 (2001) 7180-7191.
56. Greider C W, Blackburn E H. Identification of a specific telomere terminal transferase activity in Tetrahymena extracts. Cell. 1985 December;43(2 Pt 1):405-13.
57. Schmidt J C, Cech T R. Human telomerase: biogenesis, trafficking, recruitment, and activation. Genes Dev. 2015 June 1;29(11):1095-1105.
58. Nandakumar J, Cech T R. 2013. Finding the end: recruitment of telomerase to telomeres. Nat Rev Mol Cell Biol 14: 69-82.
59. Palm W, de Lange T. 2008. How shelterin protects mammalian telomeres. Annu Rev Genet 42: 301-334.
60. Masutomi K, Kaneko S, Hayashi N, Yamashita T, Shirota Y, Kobayashi K, Murakami S. Telomerase activity reconstituted in vitro with purified human telomerase reverse transcriptase and human telomerase RNA component. J Biol Chem. 2000 July 21;275(29):22568-73.
61. Pardue M L, DeBaryshe P G. Drosophila telomeres: A variation on the telomerase theme. Fly (Austin). 2008 May-June;2(3):101-10.
62. Zhang L, Rong Y S. Retrotransposons at Drosophila telomeres: host domestication of a selfish element for the maintenance of genome integrity. Biochim Biophys Acta. 2012 July;1819(7):771-5.
63. Goldbeter A l, Gerard C, Gonze D, Leloup J C, Dupont G. Systems biology of cellular rhythms. FEBS Lett. 2012 August 31;586(18):2955-65.
64. Vijai Singh. Recent advancements in synthetic biology: Current status and challenges. Gene. Volume 535, Issue 1.

65. Purcell O, Savery N J, Grierson C S, di Bernardo M A comparative analysis of synthetic genetic oscillators. J R Soc Interface. 2010 Nov 6;7(52):1503-24.
66. T. Danino, O. Mondragon-Palomino, L. Tsimring, J. Hasty .A synchronized quorum of genetic clocks. Nature, 463 (7279) (2010), pp. 326-330.
67. O. Mondragon-Palomino, T. Danino, J. Selimkhanov, L. Tsimring, J. Hasty. Entrainment of a population of synthetic genetic oscillators. Science, 333 (6047) (2011), pp. 1315-1319.
68. Aubel D, Fussenegger M. Watch the clock-engineering biological systems to be on time. Curr Opin Genet Dev. 2010 December;20(6):634-43.
69. Stricker J, Cookson S, Bennett M R, Mather W H, Tsimring L S, Hasty J. A fast, robust and tunable synthetic gene oscillator Nature. 2008 November 27;456(7221):516-9.
70. Tigges M, Marquez-Lago T T, Stelling J, Fussenegger M A tunable synthetic mammalian oscillator. Nature. 2009 January 15;457(7227):309-12.
71. Abe, T. et al. Establishment of conditional reporter mouse lines at ROSA26 locus for live cell imaging. Genesis 49,579-590 (2011).
72. Kuhn, R., Schwenk, F., Aguet, M. & Rajewsky, K. Inducible gene targeting in mice. Science. 269,1427-1429 (1995).
73. Jos Jonkers, Anton Berns. Conditional mouse models of sporadic cancer. Nature Reviews Cancer 2,251-265 (April 2002).
74. Zetsche B, Gootenberg J S, Abudayyeh O O, Slaymaker I M, Makarova K S, Essletzbichler P, Volz S E, Joung J, van der Oost J, Regev A, Koonin E V, Zhang F. Cpf1 is a single RNA-guided endonuclease of a class 2 CRISPR-Cas system. Cell. 2015 October 22;163(3):759-71.
75. McKenna, A. et al. Whole-organism lineage tracing by combinatorial and cumulative genome editing. *Science* 353, aaf7907, doi:10.1126/science.aaf7907 (2016).
76. Tsai, S. Q. et al. Dimeric CRISPR RNA-guided FokI nucleases for highly specific genome editing. *Nat Biotechnol* 32, 569-576, doi:10.1038/nbt.2908 (2014).
77. Krivega, I., Dale, R. K. & Dean, A. Role of LDB1 in the transition from chromatin looping to transcription activation. *Genes Dev* 28, 1278-1290, doi:10.1101/gad.239749.114 (2014).
78. Tu, C. P. & Cohen, S. N. 3'-end labeling of DNA with [alpha-32P]cordycepin-5'-triphosphate. *Gene* 10, 177-183 (1980).
79. Yamtich, J. & Sweasy, J. B. DNA polymerase family X: function, structure, and cellular roles. *Biochim Biophys Acta* 1804, 1136-1150, doi:10.1016/j.bbapap.2009.07.008 (2010).
80. Hurwitz, J. & Leis, J. P. RNA-dependent DNA polymerase activity of RNA tumor viruses. I. Directing influence of DNA in the reaction. *J Virol* 9, 116-129 (1972).
81. Gibb, S., Maroto, M. & Dale, J. K. The segmentation clock mechanism moves up a notch. *Trends Cell Biol* 20, 593-600, doi:10.1016/j.tcb.2010.07.001 (2010).
82. Alam, M. J. et al. Switching p53 states by calcium: dynamics and interaction of stress systems. *Mol Biosyst* 9, 508-521, doi:10.1039/c3mb25277a (2013).
83. Mondragon-Palomino, O., Danino, T., Selimkhanov, J., Tsimring, L. & Hasty, J. Entrainment of a population of synthetic genetic oscillators. *Science* 333, 1315-1319, doi:10.1126/science.1205369 (2011).
84. Tran, D. D., Corsa, C. A. S., Biswas, H., Aft, R. L. & Longmore, G. D. Temporal and Spatial Cooperation of Snail1 and Twist1 during Epithelial-Mesenchymal Transition Predicts for Human Breast Cancer Recurrence. *Molecular Cancer Research* 9, 1644-1657, doi:10.1158/1541-7786.mcr-11-0371 (2011).
85. Tran, H. D. et al. Transient SNAIL1 expression is necessary for metastatic competence in breast cancer. *Cancer Res* 74, 6330-6340, doi:10.1158/0008-5472.CAN-14-0923 (2014).
86. Klein, C. A. Parallel progression of primary tumours and metastases. *Nature reviews. Cancer* 9, 302-312, doi: 10.1038/nrc2627 (2009).
87. Schardt, J. A. et al. Genomic analysis of single cytokeratin-positive cells from bone marrow reveals early mutational events in breast cancer. *Cancer Cell* 8, 227-239, doi: 10.1016/j.ccr.2005.08.003 (2005).

We claim:

1. A cell comprising, incorporated into the cell's genome, the following constructs:
   i) a nucleic acid encoding a first sequence specific nuclease (a first DNA cutter) capable of creating a double strand break (DSB) in a sequence specific manner at a first predefined constitutively accessible target site in the genomic DNA;
   ii) a nucleic acid encoding a first DNA polymerase (a first DNA writer), wherein the first DNA writer is a template-independent DNA polymerase capable of adding a random DNA sequence directly to the genomic DNA at the DSB created by the first DNA cutter in the absence of a template;
   iii) a nucleic acid encoding a second sequence specific nuclease (a second DNA cutter) that creates a second DSB in a second sequence specific manner at a second predefined constitutively accessible target site in the genomic DNA; and
   iv) a nucleic acid encoding a second DNA polymerase (a second DNA writer), wherein the second DNA writer is a template-dependent polymerase that is able to add a second DNA sequence directly to the genomic DNA at the second DSB created by the second DNA cutter, wherein, the nucleic acid encoding the first DNA cutter and the nucleic acid encoding the first DNA writer are under the control of a first promoter, wherein the first promoter is not constitutively active and is regulated during a cell cycle, by a cellular timing signal, by a cell fate transition, or by production in the cell of a first biomolecule such that expression of the first DNA cutter and the first DNA writer linked to the first promoter occurs when the first promoter is activated; and wherein the nucleic acid encoding the second DNA cutter and the nucleic acid encoding the second DNA writer are under the control of a second promoter, wherein the second promoter is not constitutively active and is regulated during a cell cycle, by a cellular timing signal, by a cell fate transition, or by production in the cell of a second biomolecule such that expression of the second DNA cutter and the second DNA writer linked to the second promoter occurs when the second promoter is activated.

2. The cell of claim 1, wherein the first and second DNA cutters are independently selected from the group consisting of: a Protospacer Adjacent Motif (PAM)-independent Cas9*, a Cas9-related endonuclease that cuts downstream of the PAM so that the PAM is retained for subsequent barcode insertions (PAM-retaining Cas9*), a Transcription Activator-Like Effector Nuclease (TALEN) capable of recognizing ROSA26-located target, and a zinc finger nuclease.

3. The cell of claim 1, wherein the template-independent DNA polymerase is selected from the group consisting of: terminal deoxynucleotidyl transferase, DNA polymerase from Thermus aquaticus, polymerase alpha from chick embryo, rat polymerase beta, reverse transcriptase from avian myeloblastosis virus, and DNA polymerase I from Saccharomyces cerevisiae.

4. The cell of claim 3, wherein the template-independent DNA polymerase is a terminal deoxynucleotidyl transferase.

5. The cell of claim 1, wherein the template-dependent DNA polymerase is selected from the group consisting of: a human telomerase, a reverse transcriptase encoded in a Drosophila retrotransposable elements or retrotransposons engineered to have reduced processivity, and a retroviral reverse transcriptase engineered to have reduced processivity.

6. The cell of claim 5, wherein the template-dependent DNA polymerase is a human telomerase reverse transcriptase.

7. The cell of claim 1, wherein the nucleic acid encoding the first DNA cutter and the nucleic acid encoding the first DNA writer are both under the control of the same copy of the first promoter.

8. The cell of claim 7, wherein the nucleic acids encoding the first DNA cutter and the first DNA writer encode the first DNA cutter fused to the first DNA writer by a flexible linker.

9. The cell of claim 1, wherein the nucleic acid encoding the first DNA cutter and the nucleic acid encoding the first DNA writer are under the control of different copies of the first promoter.

10. The cell of claim 1, wherein the first promoter is activated by an initiation of a cell cycle, a termination of the cell cycle, an initiation of epithelial to mesenchymal transition (EMT), an initiation of mesenchymal to epithelial transition (MET), circadian rhythm, an activation of cellular invasion, an initiation of an immune reaction, a neuronal excitation, or a transformation to a cancerous state.

11. The cell of claim 1, wherein the first DNA cutter and the second DNA cutter are different from each other.

12. The cell of claim 1, wherein the first DNA cutter and the second DNA cutter are the same.

13. The cell of claim 12, wherein the first DNA cutter is a PAM-retaining Cas9* and the second DNA cutter is a PAM-retaining Cas9*.

14. The cell of claim 1, wherein the first DNA cutter is a PAM-retaining Cas9*, the second DNA cutter is a PAM-retaining Cas9*, the first DNA writer is a terminal deoxynucleotidyl transferase, and the second DNA writer is a human telomerase reverse transcriptase.

15. The cell of claim 1, wherein the first DNA writer is a terminal deoxynucleotidyl transferase and the second DNA writer is a human telomerase reverse transcriptase.

16. The cell of claim 1, wherein the cell is an animal cell or a mammalian cell.

17. The cell of claim 1, wherein the nucleic acid encoding the second DNA cutter and the nucleic acid encoding the second DNA writer are both under the control of the same copy of the second promoter.

18. The cell of claim 17, wherein the nucleic acids encoding the second DNA cutter and the gene encoding the second DNA writer encode the second DNA cutter fused to the second DNA writer by a flexible linker.

19. The cell of claim 1, wherein the nucleic acid encoding the second DNA cutter and the nucleic acid encoding the second DNA writer are under the control of different copies of the second promoter.

20. The cell of claim 1 wherein the cell is in a non-human animal.

21. A composition comprising:
i) a nucleic acid encoding a first sequence specific nuclease (a first DNA cutter) capable of creating a DSB in a sequence specific manner at a first predefined constitutively accessible target site in the genomic DNA;
ii) a nucleic acid encoding a first DNA polymerase (a first DNA writer), wherein the first DNA writer is a template-independent DNA polymerase capable of adding a random DNA sequence directly to the genomic DNA at the DSB created by the first DNA cutter in the absence of a template;
iii) a nucleic acid encoding a second sequence specific nuclease (a second DNA cutter) that creates a second DSB in a second sequence specific manner at a second predefined constitutively accessible target site in the genomic DNA; and
iv) a nucleic acid encoding a second DNA polymerase (a second DNA writer), wherein the second DNA writer is a template-dependent polymerase that is able to add a second DNA sequence directly to the genomic DNA at the second DSB created by the second DNA cutter,
wherein, the nucleic acid encoding the first DNA cutter and the nucleic acid encoding the first DNA writer are under the control of a first promoter, wherein the first promoter is not constitutively active and is regulated during a cell cycle, by a cellular timing signal, by a cell fate transition, or by production in the cell of a first biomolecule such that expression of the first DNA cutter and the first DNA writer linked to the first promoter occurs when the first promoter is activated
wherein the nucleic acid encoding the second DNA cutter and the nucleic acid encoding the second DNA writer are under the control of a second promoter, wherein the second promoter is not constitutively active and is regulated during a cell cycle, by a cellular timing signal, by a cell fate transition, or by production in the cell of a second biomolecule such that expression of the second DNA cutter and the second DNA writer linked to the second promoter occurs when the second promoter is activated.

22. The composition of claim 21, wherein the nucleic acids encoding the first DNA cutter and the first DNA writer encode the first DNA cutter fused to the first DNA writer by a flexible linker, and/or the nucleic acidz encoding the second DNA cutter and the second DNA writer encode the second DNA cutter fused to the second DNA writer by a flexible linker.

* * * * *